(12) United States Patent
Lowdell

(10) Patent No.: US 8,735,148 B2
(45) Date of Patent: May 27, 2014

(54) PRESERVED COMPOSITIONS OF ACTIVATED NK CELLS AND METHODS OF USING THE SAME

(75) Inventor: Mark Lowdell, Beaumont-Cum-Moze (GB)

(73) Assignee: UCL Business PLC, London (GB)

( * ) Notice: Subject to any disclaimer, the term of this patent is extended or adjusted under 35 U.S.C. 154(b) by 621 days.

(21) Appl. No.: 12/833,694

(22) Filed: Jul. 9, 2010

(65) Prior Publication Data

US 2011/0014162 A1 Jan. 20, 2011

Related U.S. Application Data

(60) Provisional application No. 61/224,771, filed on Jul. 10, 2009, provisional application No. 61/301,529, filed on Feb. 4, 2010.

(51) Int. Cl.
*C12N 5/00* (2006.01)
*C12N 5/02* (2006.01)
*C12N 5/07* (2010.01)

(52) U.S. Cl.
USPC ........... 435/325; 435/326; 435/366; 435/372; 424/93.7

(58) Field of Classification Search
None
See application file for complete search history.

(56) References Cited

U.S. PATENT DOCUMENTS 8,257,970 B2 * 9/2012 Lowdell ................... 435/325
2012/0328587 A1 * 12/2012 Lowdell ................. 424/93.71

FOREIGN PATENT DOCUMENTS

WO    WO 2006097743 A2 *  9/2006

OTHER PUBLICATIONS

Kottaridis et al. (2008) Blood 112(11): 2901.*

* cited by examiner

*Primary Examiner* — Lisa J Hobbs
(74) *Attorney, Agent, or Firm* — Todd Lorenz; Arnold & Porter LLP

(57) ABSTRACT

Disclosed herein are activated NK cells that exhibit durable and prolonged activity in the absence of the activating agent and retain their activated state after preservation. Methods of administrating the NK cells to a patient do not require co-administration of the activating agent, and thus, pharmaceutical compositions comprising the NK cells may remain substantially free of the activating agent.

18 Claims, 8 Drawing Sheets

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
atgggggcac cgtggggctc gccgac                26

<210> SEQ ID NO 2
<211> LENGTH: 24
<212> TYPE: DNA
<213> ORGANISM: artificial
<220> FEATURE:
<223> OTHER INFORMATION: primer

<400> SEQUENCE: 2
agtggcgagc ttggtcgacc ggtt                24

PRESERVED COMPOSITIONS OF ACTIVATED NK CELLS AND METHODS OF USING THE SAME

CROSS-REFERENCE TO RELATED APPLICATIONS

This application claims priority from U.S. Provisional Application Ser. No. 61/224,771 (filed Jul. 10, 2009) and U.S. Provisional Application Ser. No. 61/301,529 (filed Feb. 4, 2010), each of which is incorporated herein by reference in its entirety.

FIELD OF INVENTION

The present invention relates generally to preserved populations of natural killer cells exhibiting a durable activation state, pharmaceutical compositions comprising such activated NK cells, and methods of using the same.

BACKGROUND OF THE INVENTION

Adoptive immunotherapy of cancer contemplates direct stimulation of the host immune response to tumor through vaccination with specific tumor cells and/or administration of more general immune stimulants. Several factors can impede an adequate anti-tumor immune response, however, including the lack of a suitable tumor-associated antigen, defective antigen processing, production of immunologically suppressive factors by the tumor, and the like.

Adoptive immunotherapy attempts to overcome tumor-mediated host immune suppression by administering immunologically active cells or antibodies directly to the tumor-bearing host. In adoptive cell therapy approaches, immune effector cells are isolated from a tumor-bearing host and activated and/or expanded ex vivo prior to reinfusion. Autologous NK cells, for example, have been activated ex vivo with recombinant interleukin-2 (IL-2) to enhance CD56+ natural killer (NK) cell cytotoxicity (Lather et al. (1985) *Journal of Immunology* 134, 794-801) and generate lymphokine activated killer (LAK) cells, which are capable of killing fresh autologous and allogeneic human tumor cells in vitro. (Rayner, et al. (1985) *Cancer* 55, 1327-1333). The administration of LAK cells, typically in combination with systemic IL-2 infusion, has been repeatedly investigated as an adoptive immunotherapy for human cancer.

Unfortunately, however, these LAK cell therapies have met with only limited success in the clinic. Autologous cells must first be obtained from the patient and successfully expanded ex vivo to a cell count sufficient for therapy. Moreover, the LAK cells must be continuously exposed to IL-2 in order to maintain their activated state and, accordingly, effective clinical protocols generally require high-dose systemic IL-2 administration in conjunction with the cell therapy. Although some anti-tumor effects were obtained in some patients, toxicities resulting from the IL-2 co-administration were a significant problem (Vieweg et al. (1995) *Cancer Investigation* 13:193-201), including fever, chills, malaise, arthralgias, myalgias, and weight gain from fluid retention (Lotze, et al. (1985) *J. Immunology* 135: 2865-2875).

Successful implementation of LAK cell therapy is also hampered by the inability to employ the activated LAK cells other than in real-time, individualized protocols. In particular, special equipment and dedicated laboratories are necessary to isolate, expand and reinfuse each patient's cells. Moreover, LAK cell activity is significantly impaired within twelve hours after removal of IL-2 and, accordingly, once activated, the LAK cells must be promptly infused before the activation state is lost. Significantly, preservation of LAK cells necessitates that LAK cells be prepared for administration by re-stimulation with IL-2 to re-establish the activated state. (Kawai et al. (1988) *Transfusion* 28:531-5; Schiltz et al. (1998) *J. Immunother.* 20:377-86). Accordingly, the administration of LAK cells for the immunotherapy of cancer has had limited clinical impact and acceptance, requiring expensive, individualized and labor intensive methods for isolation and expansion, and real-time administration to avoid loss of activation.

What is needed, therefore, are activated immune effector cell populations having more reliable and durable activity that can better facilitate the coordination of cellular therapy with donor care. Ideally, these cells can sustain their activated state despite preservation, and without continuous exposure to the activating agent and/or co-administration of undesirable and/or clinically toxic agents, such that more general clinical applications might be possible.

SUMMARY OF INVENTION

The present invention provides preserved populations of activated NK cells having significant anti-tumor activity that exhibit a surprisingly durable activation state despite prior preservation, and even in the absence of the activating agent (e.g., after termination of contact with the activating agent and/or without continued exposure to or reactivation with the activating agent). Significantly, and unlike LAK cells, the activated NK cells of the subject invention can be administered to a patient directly after preservation and without the need for reactivation, and furthermore without the need for co-administration of the activating agent itself, thereby providing clinicians with a sustainable and ready-to-use cell therapy product that also avoids potential toxicities attendant with co-administration of the activation agent.

Moreover, the subject cell populations can be effectively employed across allogeneic barriers and, significantly, are capable of transferring tumoricidal abilities to endogenous host NK cells upon adoptive transfer, thereby producing an NK cell activation cascade in vivo. Accordingly, the activated NK cell populations provided herein can be employed more generally and more practically in both active and passive immunotherapy settings, and without the need for personalized treatment regimens and/or real-time administration protocols.

Accordingly, in one aspect, the invention provides pharmaceutical compositions of activated NK cells. The compositions may be suitable for direct administration to a patient. The compositions may be substantially free of activating agent. The activated NK cells may have been previously preserved. In use, the activated NK cells may, after any preservation, subsequently be prepared for administration without reactivation or contact with the activating agent. In embodiments, the compositions comprising previously preserved activated NK cells are suitable for direct administration, and are free of activating agent. The composition may be, and usually is, for administration without co-administration (whether simultaneous, separate or sequential) of the activating agent.

In other aspects, there are provided (i) a population of activated NK cells for therapeutic use e.g. for use in the treatment of a cancer, and (ii) the use of a population of activated NK cells for the manufacture of a medicament e.g. for use in the treatment of a cancer. The population may be preserved. The population may be free of activating agent. The population may include a pharmaceutically acceptable medium or carrier. The population may be reconstituted into a pharmaceutical composition. The description herein of the pharmaceutical compositions of the invention therefore applies mutatis mutandis to the cell populations of the invention, for example the NK cells may be obtainable by activation with CD15+ LAK-resistant tumor cells. Preferably, the NK cells overexpress CD69 and/or CD25 in comparison with resting NK cells and exhibit a durable and prolonged anti-tumor activity despite the absence of the activating agent. Accordingly, in one embodiment the previously-activated NK cells are CD69+ and/or CD25+. In a further embodiment, the activated NK cells contemplated for use herein also gain expression of CD15 and lose expression of CD16 after activation. Accordingly, the subject NK cells are more preferably also CD15+ and $CD16^{low}$. These $CD69+CD25+CD16^{low}CD15+$ NK cells will typically comprise at least about 50% of the cell population, more preferably at least about 60, 70 or 80% of the cell population, and most preferably at least about 90, 95 or 98% of the cell population.

In one embodiment, the disclosed pharmaceutical compositions comprise activated NK cells that are autologous to the patient. In another embodiment, the pharmaceutical compositions comprise activated NK cells that are autologous to the patient and allogeneic to the patient. In another embodiment, the pharmaceutical compositions comprise activated NK cells that are allogeneic to the patient. In another embodiment, the pharmaceutical compositions comprise activated NK cells that are allogeneic to each other.

Suitable preservation techniques that may advantageously be employed in conjunction with the subject invention include cell culture, refrigeration, and cryopreservation.

In a preferred embodiment, the activated NK cells are cryopreserved (e.g., in nitrogen vapor) for at least about 1 day, e.g., for at least 1 week, e.g., for at least about 4 weeks, e.g., for at least about 3 months, e.g., for about 6 months, e.g., for at least about one year, e.g., for at least about five years, etc. In one embodiment, the activated NK cells are preserved in a cryocyte bag at a cell density of between about $1\times10^6$ and $5\times10^7$ cells/mL, more preferably between about $1\times10^7$ and $2\times10^7$ cells/mL, in a medium comprising DMSO and HSA. In one embodiment, the cryopreserved NK cells are prepared for administration by thawing. In one embodiment, the activated NK cells are thawed in the absence of an activating agent, and administered immediately after thawing. The invention includes, therefore, a method for making a ready-to-use medicament in the form of an infusible formulation which is free of agent for activating NK cells, the method comprising, or consisting of, thawing cryopreserved activated NK cells substantially free of activating agent, the formulation being for use in treating a cancer without co-administration (whether simultaneous, separate or sequential) of the activating agent. The infusible formulation in this embodiment is ready for immediate use without any further processing.

In one embodiment, the NK cells are activated by incubating with CD15+ LAK-resistant tumor cells before preservation. In one embodiment, the CD15+ LAK-resistant tumor cell is selected from the group consisting of CTV-1, MV4-11, SEM, sublines thereof, and combinations thereof. In one embodiment, the CD15+LAK-resistant tumor cells comprise CTV-1 cells. In another embodiment, the CD15+ LAK-resistant tumor cells comprise MV4-11 cells. In another embodiment, the CD15+ LAK-resistant tumor cells comprise SEM cells.

Also provided herein are methods for preparing and administering the subject compositions, comprising 1) obtaining autologous and/or allogeneic NK cells, 2) activating said NK cells with an activating agent comprising CD15+ LAK-resistant tumor cells, 3) preserving the activated NK cells in the absence of the activating agent, 4) preparing the activated NK cells for administration after preservation, e.g., thawing after cryopreservation, in a pharmaceutically acceptable carrier substantially free of activating agent, and 5) administering the activated NK cells to a patient in need thereof without co-administering the activating agent itself, either simultaneously or sequentially. In preferred embodiments, at least about 50%, more preferably at least about 60, 70 or 80%, and most preferably at least about 90, 95 or 98% of the activated NK cells are characterized as $CD69+CD25+CD16^{low}CD15+$. In one embodiment, the preservation technique employed is cryopreservation, and the activated NK cells are administered to the patient immediately after thawing, with or without resuspension.

In one embodiment, the activated NK cells are autologous to the patient. In another embodiment, the activated NK cells comprise NK cells that are autologous to the patient and NK cells that are allogeneic to the patient. In another embodiment, the activated NK cells are allogeneic to the patient. In another embodiment, the activated NK cells are allogeneic to each other.

Also provided is a method of stimulating endogenous NK cell activity, e.g., endogenous anti-tumor activity, in a patient in need thereof, e.g., a tumor-bearing patient, comprising administering to said patient a population of exogenous NK cells previously activated to overexpress CD69 and/or CD25 in comparison with resting NK cells, and preferably reduce expression of CD16 and gain expression of CD15, wherein said NK cells exhibit durable activity in the absence of an activating agent. As detailed herein, the $CD69+CD25+CD16^{low}CD15+$ activated NK cells of the subject compositions can be directly administered to patients in need thereof without repeated or continuous contact with the activating agent, and moreover also without co-administration of the activating agent to the patient, as is the case with LAK cells. In one embodiment, the exogenous NK cells are activated by contacting the NK cells with CD15+ LAK-resistant tumor cells, e.g., CTV-1 tumor cells, MV4-11 tumor cells, SEM tumor cells, and the like. In a preferred embodiment, the CD15+ LAK-resistant tumor cells are CTV-1 cells.

In one method disclosed herein, the cell population comprises exogenous NK cells that are autologous to the patient. In another method, the cell population comprises exogenous NK cells that are autologous to the patient and exogenous NK cells that are allogeneic to the patient. In another method, the cell population comprises exogenous NK cells that are allogeneic to each other. In another method, the cell population comprises exogenous NK cells that are allogeneic to the patient and NK cells that are allogeneic to each other.

In one embodiment, the cell population is preserved after activation and prior to administration to said patient. In a preferred embodiment, the cell population is cryopreserved. In an exemplary embodiment, the method further comprises the step of thawing said population prior to the step of administering. Significantly, as demonstrated herein, the subject invention does not require reactivation after preservation and before administration to the patient, and also does not require co-administration of the activating agent.

BRIEF DESCRIPTION OF THE DRAWINGS

FIG. 1 demonstrates that CD15+ NK-resistant tumor cells prime resting NK cells to lyse NK-resistant tumor cells.

FIG. 2 demonstrates blockade of NK cell priming by anti-CD15.

FIG. 4 shows the percentage of NK cells isolated from 9 healthy patients that expressed CD16 (% CD16 positive; y-axis) after overnight incubation in the absence (NK o/n; x-axis) or presence of CTV-1 cells (NK/CTV-1) at a stimulator:responder ratio of 2:1. Each square or triangle represents one of nine healthy donors from which the NK cells were isolated. The proportion of CD16+ NK cells remained stable in the absence of tumor stimulation. In contrast, CTV-1 mediated priming led to a significant loss of CD16 expression (p<0.01).

FIG. 5 shows intracellular phosphorylation following stimulation with CTV-1. FIG. 5C is the representative plot of 3 experiments.

FIG. 6 demonstrates NK activation following CTV-1 or IL-2 stimulation. FIGS. 6 and 6G are histograms that show the number of NK cells (y-axis) expressing cell surface CD69 (FIGS. 6B, 6C, and 6D) or intracellular IFN-γ (FIGS. 6E, 6F, and 6G) after incubation overnight in the absence of any activating agent (FIGS. 6B and 6E), in the presence of CTV-1 cells (FIGS. 6C and 6F), or in the presence of IL-2 (FIG. 6D and FIG. 6G). The vertical bar in each histogram represents the maximum fluorescence of the specific isotype-matched negative control.

FIG. 7A is a dot plot of peripheral blood mononuclear cells that stimulated with CTV-1 cell lysate for 20 hours and incubated with anti-CD56-FITC and anti-CD3-APC antibodies before immunomagenteic sorting for NK cells. FIG. 7B is a dot plot of periphperal blood mononuclear cells stimulated with CTV-1 cell lysate for 20 hours and incubated with anti-CD56-FITC and anti-CD3-APC antibodies after immunomagnetic sorting for NK cells. In each dotplot, NK cells are found in the region denoted as R2, NKT cells are found in the region denoted as R3, CTV-1 lysate is found in the region denoted as R4, and T cells are found in the region denoted R5. FIG. 7C shows lysis of RAJI cells (% specific lysis; y-axis) by NK cells freshly primed with CTV-1 lysate (fresh; x-axis) and NK cells previously primed with CTV-1 lysate that had been cryopreserved for 14 days and thawed prior to incubation with RAJI cells (post-thaw; x-axis).

DETAILED DESCRIPTION

Figure 1A:
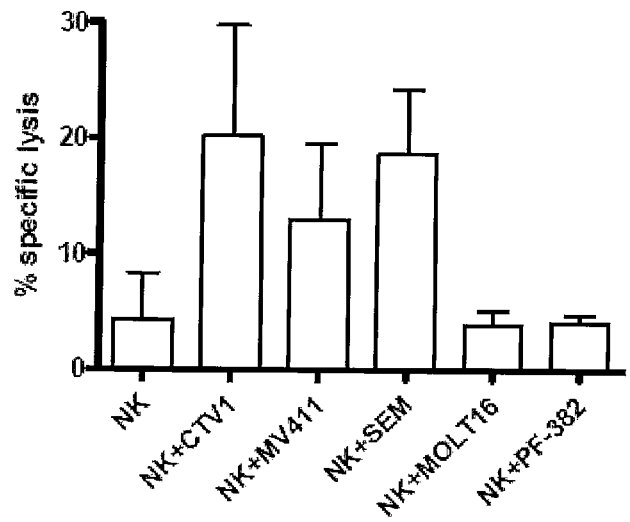
FIG. 1A shows the lysis of NK-resistant RAJI cells (% specific lysis; y-axis) by resting NK cells that were unstimulated (NK; x-axis), NK cells incubated with one of three NK-resistant positive CD15+ leukemic cells: CTV-1 (NK+CTV1; x-axis), MV-411 (NK+MV411; x-axis) or SEM (NK+SEM; x-axis), or NK cells incubated with one of two CD15-ve tumor cells: MOLT-16 (NK+MOLT16; x-axis) or PF-382 (NK+PF-382).

The present invention relates to the unexpected finding that, in contrast to LAK cells, the activated NK cell populations provided herein exhibit durable activity even in the absence of activating agent and, significantly, retain their anti-tumor activity despite intervening preservation for a prolonged period of time. The preserved populations of previously-activated NK cells described herein can be effectively used across allogeneic barriers and, also surprisingly, are able transfer tumoricidal abilities to endogenous host NK cells upon adoptive transfer into a tumor-bearing host, thereby producing an NK activation cascade in vivo. Accordingly the activated NK cell populations provided herein can be employed more generally and more practically in both active and passive immunotherapy settings, and without the need for personalized treatment regimens, real-time administration protocols and/or co-administration of otherwise undesirable and/or toxic activating agents.

In accordance with the present invention, previously-preserved cell populations comprising NK cells that have been activated with CD15+ LAK-resistant tumor cells exhibit durable and prolonged activity even after preservation in the absence of an activating agent, and without reactivation or contact with the activating agent after preservation. Accordingly, preservation methods such as cell culture, refrigeration, cryopreservation, etc., can be employed without significant loss of activity and the activated cells may be administered to a patient immediately after preservation, e.g., preparing the cells for administration does not need to include exposing the cells to the activating agent for the cells to be therapeutic, and the activated cells need not be co-administered in conjunction with the activating agent itself. Disclosed herein are pharmaceutical compositions comprising activated NK cells prepared for administration after preservation, and corresponding methods of use.

"Previously-activated" as used herein refers to prior contact and/or exposure to (e.g., incubation with) an activating agent, e.g., CD15+ LAK-resistant tumor cells, and preferably a CD15+ LAK-resistant tumor cell preparation.

"Durable" as used herein in the context of NK cell activation refers to the ability of a previously activated NK cell to maintain lytic activity, e.g., anti-tumor activity, in the absence of continued or repeated contact with an activating agent for an extended period of time, e.g., at least about 6-8 hours, more preferably at least about 10-12 hours, still more preferably at least about 12 to 14 hours.

Natural Killer (NK) Cells

NK cells are a subset of peripheral blood lymphocytes defined by the expression of CD56 or CD16 and the absence of the T cell receptor (CD3). They recognize and kill transformed cell lines without priming in an MHC-unrestricted fashion.

NK cells represent the predominant lymphoid cell in the peripheral blood for many months after allogeneic or autologous stem cell transplant and they have a primary role in immunity to pathogens during this period (Reittie et al (1989) Blood 73: 1351-1358; Lowdell et al (1998) Bone Marrow Transplant 21: 679-686). The role of NK cells in engraftment, graft-versus-host disease, anti-leukemia activity and post-transplant infection is reviewed in Lowdell (2003) Transfusion Medicine 13:399-404.

Human NK cells mediate the lysis of tumor cells and virus-infected cells via natural cytotoxicity and antibody-dependent cellular cytotoxicity (ADCC).

Human NK are controlled by positive and negative cytolytic signals. Negative (inhibitory) signals are transduced by C-lectin domain containing receptors CD94/NKG2A and by some Killer Immunoglobulin-like Receptors (KIRs). The regulation of NK lysis by inhibitory signals is known as the "missing self" hypothesis in which specific HLA-class I alleles expressed on the target cell surface ligate inhibitory receptors on NK cells. The down-regulation of HLA molecules on tumor cells and some virally infected cells (e.g. CMV) lowers this inhibition below a target threshold and the target cells may become susceptible to NK cell-mediated lysis if the target cells also carry NK-priming and activating molecules.

Inhibitory receptors fall into two groups, those of the Ig-superfamily called Killer Immunoglobulin-like Receptors (KIRs) and those of the lectin family, the NKG2, which form dimers with CD94 at the cell surface. KIRs have a 2- or 3-domain extracellular structure and bind to HLA-A, -B or -C. The NKG2/CD94 complexes ligate HLA-E.

Inhibitory KIRs have up to 4 intracellular domains which contain ITIMs and the best characterized are KIR2DL1, KIR2DL2 and KIR2DL3 which are known to bind HLA-C molecules. KIR2DL2 and KIR2DL3 bind the group 1 HLA-C alleles while KIR2DL1 binds to group 2 alleles. Certain leukemia/lymphoma cells express both group 1 and 2 HLA-C alleles and are known to be resistant to NK-mediated cell lysis As regards to positive activating signals, ADCC is thought to be mediated via CD16, and a number of triggering receptors responsible for natural cytotoxicity have been identified, including CD2, CD38, CD69, NKRP-1, CD40, B7-2, NK-TR, NKp46, NKp30 and NKp44. In addition, several KIR molecules with short intracytoplasmic tails are also stimulatory. These KIRs (KIR2DS1, KIR2DS2 and KIR2DS4) are known to bind to HLA-C; their extracellular domains being identical to their related inhibitory KIRs. The activatory KIRs lack the ITIMs and instead associate with DAP12 leading to NK cell activation. The mechanism of control of expression of inhibitory versus activatory KIRs remains unknown.

The NK cells of the present invention may be autologous or allogeneic NK cells.

"Autologous" NK cells are cells derived from the patient, e.g., a tumor-bearing host.

"Allogeneic" NK cells are derived from another, non-genetically identical individual. If the NK cells are derived from an identical twin, they may be termed "syngeneic".

Donor NK cells may be HLA-KIR matched or mismatched. The present inventors have shown that the degree of matching between the NK cells and target tumor cells is of no significance.

Activating Agents

Disclosed herein is a preserved population of previously-activated NK cells that exhibit durable activity, i.e., that retain the activated state after preservation or in the absence of the activating agent. Accordingly, a skilled artisan will recognize that activating agent as used herein refers to any agent that activates NK cells (e.g., increases the lytic activity of NK cells) to overexpress CD69 and/or CD25 in comparison with resting NK cells, and more preferably to also gain CD15 expression and lose CD16 expression. As demonstrated herein, NK cells activated according to the present invention retain their activated state after termination of contact with the activating agent, e.g., during preservation in the absence of the activating agent.

The term "activating" is used synonymously with the term "stimulating" in this section, and throughout the document.

The present invention also provides a method for determining whether an agent is an activating agent as disclosed herein, the method having the following steps:

(i) contacting the agent with a NK cell to activate the NK cell;

(ii) preserving the activated NK cell;

(iii) contacting the activated NK cell from step (ii) with a target cell resistant to lysis by non-activated NK cells;

(iv) determining whether the target cell is lysed by the NK cell from step (ii); wherein the activated NK cell is not contacted with or exposed to the activating agent at any time during or after preservation (e.g., remains substantially free of the activating agent during and/or after preservation).

Optionally, the activated NK cells from step (i) or step (iv) above can be analyzed to determine expression of CD69, CD25, CD16 and CD15, wherein appropriate activating agents will produce NK cells that overexpress CD69 and CD25 in comparison with resting NK cells, and lose expression of CD16 and gain expression of CD15 after activation.

It is thus readily determinable for a skilled person to establish whether a given agent has the capacity to act as an activating agent as described herein.

As described in the Examples, certain tumor cells, e.g., CD15+ LAK-resistant tumor cells, have the capacity to stimulate NK cells to increase their capacity to lyse tumor cells. Stimulated NK cells have been shown to be capable of lysing "NK-resistant" tumor cell (i.e. tumor cells resistant to lysis with unstimulated NK cells). Furthermore, such stimulated NK cells retain their activated state after preservation in the absence of CD15+ LAK-resistant tumor cells, and thus, do not need reactivation by subsequent contact with the CD15+ LAK-resistant tumor cell after preservation. Accordingly, in one embodiment, an activating agent as disclosed herein is a CD15+ LAK-resistant tumor cell.

"CD15" as used herein refers to the ligand for CD2 that is structurally associated with CD15 and that is essential to prime resting NK cells. As used herein, "CD15" may also refer to the product of GeneID:2526, the official name of which is FUT4, and of which is also known as ELFT, FCT3A, FUTIV, and FUC-TIV. The product of GeneID:2526 transfers fucose to N-acetyllactosamine polysaccharides to generate fucosylated carbohydrate structures. It also catalyzes the synthesis of non-sialylated antigen, Lewis x (CD15). Accordingly, a cell that is "CD15+" expresses a ligand for CD2

Tumor cell lines are generally killed by LAK cells. However, a LAK-resistant tumor cell markedly evades lysis by LAK cells. Non-limiting examples of LAK-resistant tumor cells include CTV-1 cells, MH1354 cells, OKM-24 cells, MV4-11 cells, SEM cells, etc.

CD15+ LAK-resistant tumor cells capable of activating NK cells such that the NK cells retain their activated state after preservation even in the absence of the activating tumor cells include CTV-1 cells, MV4-11 cells, SEM cells, sublines thereof, or combinations thereof. Accordingly, in one embodiment, the activating agent is a CTV-1 cell. This cell line is commercially available, for example from the Deutsche Sammlung Mikroorganismen Zellkulturen GmbH (DSMZ). In one embodiment, the activating cell is obtained from a CTV-1 subline. In another embodiment, the activating agent is a MV4-11 cell. This cell line is also commercially available, e.g., from the American Type Culture Collection (ATCC Number CRL-9591) (Lange, et al. (1987) *Blood* 70:192-199; Santoli, et al. (1987) *J. Immunol.* 139:3348-3354). In another embodiment, the activating agent is an SEM cell. This cell line is also commercially available, e.g., from DSMZ (DSMZ No. ACC456) (Greil, et al. (1994) *Br. J. Haemotol.* 86:275-83; Reichel, et al. (1998) *Oncogene* 17:3035-44; Drexler, et al. (2004) *Leukemia* 18:227-232).

It is anticipated that other tumor cells will also have the capacity to activate NK cells such that the NK cells retain their activated state after preservation in the absence of CD15 LAK-resistant tumor cells. The present invention also provides a method for determining whether a tumor cell preparation is an activating agent as disclosed herein, the method having the following steps:

(i) contacting the tumor cell preparation with a NK cell;
(ii) storing the NK cell;
(iii) contacting the NK cell from step (ii) with a target cell resistant to lysis by non-activated NK cells;
(iv) determining whether the target cell is lysed by the NK cell from step (ii); wherein the activated NK cell is not contacted with or exposed to the tumor cell preparation at any time after preservation (e.g., remains substantially free of the activating agent during and after preservation).

It is thus possible for a skilled person to establish whether a given tumor cell preparation has the capacity to act as an activating agent and to screen known tumor cells for this activity.

In one embodiment, the activating tumor cell preparation may be a tumor cell line, e.g., may consist of or comprise a population of intact tumor cells, e.g., CTV-1 cells, SEM cells, MV-411 cells, or combinations thereof, which are preferably rendered nonviable, e.g., by fixation or irradiation.

In one embodiment, the tumor cell preparation may consist of or comprise a tumor cell lysate preparation. For example, a cell lysate preparation may be made by standard fixation techniques (such as using paraformaldehyde). Fixation has the advantage that the preparation is stabilized, has a much longer "shelf-life" and is easier to store. A suitable cell lysate preparation may also be made by repeated cycles of freeze-thawing, in combination with DNAse treatment. Such a preparation may be considered to have increased safety as it reduces the likelihood of contamination associated with prions etc.

The CD15+ LAK-resistant tumor cells may be irradiated prior to use, by standard techniques. Lysate preparations have the advantage over preparations comprising intact tumor cells as they avoid the risk of transferring potentially malignant tumor cells to the patient. In one embodiment, the activating tumor cell preparation consists of or comprises CTV-1 lysate.

The CD15+ LAK-resistant tumor cell may be or comprise an entity (such as a protein) derivable from a tumor cell. The CD15+ LAK-resistant tumor cell may, for example, comprise a recombinant protein. The protein may be derivable from CTV-1 cells, MV4-11 cells, SEM cells, sublines thereof, or a combination thereof.

The CD15+ LAK-resistant tumor cell and the NK cell preparation may be brought together by, for example, co-culturing (where intact tumor cells are used). The "activation time" will depend on the nature of the cell preparations and the contact conditions, but may commonly be 12-24 hours, perhaps 20 hours.

The present inventors have shown that pre-incubation of NK cells with a CD15+ LAK-resistant tumor cell (such as CTV-1 cells, MV4-11 cells, SEM cells, combinations thereof, sublines thereof, etc.) causes rapid upregulation of CD69 on the NK cells. They have also shown (using labelled CD69) that tumor cells which are lysable by activated NK cells express CD69 ligand (CD69L), but this expression is absent from cells which are not lysed (such as B cells). The presence of recombinant CD69 inhibits the capacity of activated NK cells to lyse tumor cells, presumably because it blocks interaction with CD69L on the tumor cells.

In addition to CD69, the IL-2 receptor, CD25, is also upregulated on NK cells after contact with CTV-1. In contrast, CD25 is downregulated in conjunction with NK activation by IL-2. Accordingly, in one embodiment the activating agents contemplated for use herein also produce an activated NK cell population that is CD69+ and/or CD25+.

In a further embodiment, contact with CTV-1 results in the transfer of CD15 to the activated NK cells (e.g., NK cells gaining CD15), and the reduction of CD16 expression from the NK cell after activation. Accordingly, in further embodiments, the activating agents contemplated for use herein also produce an activated NK cell population that is also CD15+ and/or CD16$^{low}$.

Preservation

The terms "preservation" and "preserved" as used herein refer generally to the continued maintenance of a cellular composition in viable form, such that the cellular composition may be prepared for administration to a subject, e.g., a human patient, after such preservation. As disclosed herein, the population of activated NK cells are generally preserved in the absence of the activating agent and exhibit durable activity, i.e., do not need re-stimulation with an activating agent to provide therapeutic benefit. Although unnecessary for the activated NK cells to exhibit durable activity, and less preferably, a population of activated NK cells may also be preserved in the presence of the activating agent.

The population of activated NK cells as described herein may be preserved according to any well known method, see, e.g., U.S. Pat. Nos. 7,270,946; 7,150,991; 6,921,633; Kanias and Acker (2006) *Cell Preservation Technology* 4:253-277; etc., each of which is incorporated herein in its entirety by reference. In one embodiment, the population of activated NK cells described herein is preserved by a method selected from the group consisting of cell culture, refrigeration and cryopreservation. In a preferred embodiment, the NK cell population described herein is preserved by cryopreservation.

During and most preferably after preservation the population of activated NK cells is preferably substantially free of the activating agent. A population of activated NK cells substantially free of the activating agent may be obtained using well-known methods. For example, activated NK cells may be isolated from the activating agent by density gradient separation and washing or by immunomagnetic selection of CD56+ NK cells and subsequent washing or combinations of the above.

Upon obtaining a population of activated NK cells substantially free of the activating agent, the activated NK cells may be preserved by cell culture, refrigeration, or cryopreservation. In one embodiment, the activated NK cells are preserved by cell culture. Generally, preservation by cell culture comprises suspending the previously-activated NK cells in a medium suitable to maintain the viability of the activated NK cells and incubating the suspension in a physiologically relevant environment, e.g., 37° C. and about 7% $CO_2$. A skilled artisan will recognize that many different well-known media are suitable to maintain the viability of the activated NK cells. In one embodiment, the population of activated NK cells are cultured in chemically defined medium. "Chemically-defined" as used herein refers to culture media of known chemical composition, both quantitatively and qualitatively, with no deliberately added uncharacterized supplements, even though such a medium may contain trace contaminants in its components. A chemically-defined medium necessarily lacks animal serum, feeder cells such as stromal cells, and cell-based extracellular matrices derived from, e.g., fibroblasts and the like. After being preserved by cell culture, the activated NK cells may be prepared for administration without exposing the cells to the activating agent.

Generally, preservation by refrigeration comprises suspending the activated NK cells in a medium (e.g., chemically-defined medium) suitable for maintaining the viability of the cells and incubating the suspension at about 4° C. After preservation by refrigeration, the activated NK cells may be prepared for administration without exposing the cells to the activating agent.

A variety of media and protocols for cryopreserving cells, including vitification, are known in the art. See, e.g., Strong D M et al. (1982) *J. Clin. Immunol.* 2:214-221. Generally the cells may be concentrated, suspended in a freeze medium comprising a cryoprotectant and/or stabilizer, portioned into an appropriate freezing container, cooled at a rate that minimizes damage to the frozen cells and maximizes recovery, and cryopreserved, e.g., at −70° C. or less, e.g., −80° C. or less, e.g., −135 C or less, in liquid nitrogen, or in the vapor phase of liquid nitrogen.

After obtaining activated NK cells substantially free of the activating agent, the NK cells may be resuspended in cryoprotectant or freeze medium. Cells are generally cryopreserved at a cell density different than that at which they are cultured. In one embodiment, previously-activated NK cells are cryopreserved at a cell density of between about $5\times10^6$ cell/mL freeze medium to about $2\times10^7$ cell/mL freeze medium. In a preferred embodiment, the previously-activated NK cells are cryopreserved at $10\times10^6$ cell/mL freeze medium.

Freeze medium generally comprises culture medium, a cryoprotectant, serum, and optionally a stabilizer. The cells can be preserved in any cryoprotectant known in the art. For example, the cryoprotectant can be dimethyl sulfoxide (DMSO) or glycerol. In some embodiments, the freezing medium comprises DMSO from about 5-10%, 10-90% serum albumin, and 50-90% culture medium. In some embodiments, the cryopreservation medium will comprise about 7.5% DMSO, about 42.5% serum albumin, and about 50% culture medium. The cells may also be preserved in any stabilizer known in the art. For example, the stabilizer may be methyl cellulose or serum. Other additives useful for preserving cells include, by way of example and not limitation, disaccharides such as trehalose (Scheinkonig, C. et al., *Bone Marrow Transplant.* 34(6):531-6 (2004)), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well known and described in the art (see, e.g., Broxmeyer, H. E. et al., *Proc. Natl. Acad. Sci. USA* 100(2):645-650 (2003)).

Prior to freezing, the activated NK cells may be portioned into several separate containers to create a cell bank. The cells may be preserved, for example, in glass or plastic, in a vial, tube, or bag, etc. When the cells are needed for future use, a portion of the cryopreserved cells (from one or more containers) may be selected from the cell bank, and prepared for administration. This may be advantageously done for multiple donors in a proactive and systematic fashion to create an activated NK cell bank for subsequent use. In preferred embodiments, the donor cells are activated prior to cryopreservation as described herein, and can be subsequently used for treatment of the donor, members of the donor's family, and/or other unrelated third parties in accordance with the teachings provided herein. In one embodiment, preparing the activated NK cells for administration after preservation does not include exposing the cells to an activating agent.

It is generally well known that cryopreservation of different cell types may be influenced by cooling rate. For example, overly fast cooling rates can cause lethal intracellular formation of ice crystals. Conversely, overly slow cooling rates can result in osmotic shock injury to cells. Research has shown that for most biological cells, there is a specific cooling rate that may be considered optimal for the cell type. Methods of determining the optimal cooling rates for the activated NK cells are well-known to a skilled artisan. See, e.g., Fujiwara et al. (1986) *J. Immunol. Methods* 90:265-73.

In one embodiment, the activated NK cell population herein is frozen at a rate of about −1° C./minute to about −3° C./minute, preferably at −1° C./minute. See, e.g., Locke et al. (1984) *Psychosomatic Med.* 46: 441-453. In another embodiment, the activated NK cell population as described herein is cooled at different rates at different phases, e.g., at a rate of −1 C/minute to −2°/C in while in liquid phase, at a rate of about −5° C. during the phase change, and at a rate of −2° C./minute to −3° C. in solid phase. See, e.g., Fujiwara S. et al. (1986) *J. Immunol. Methods* 90:265-273. In another embodiment, the cells may be cooled to −4° C. at a rate of −1° C./minute, then to −40° C. at a rate of −25° C./minute, then warmed to −12° C. at a rate of 15° C./minute, then cooled to −40° C. at a rate of −1° C./minute, and then cooled to −70° C. at a rate of −10° C./minute. See, e.g., Schmidt-Wolf et al. (1989) *J. Immunol. Methods* 125: 185-189. In a preferred embodiment, the cells are cooled from 4° C. to −30° C. at a rate of −1° C./minute, and subsequently coiled to −100° C. at a rate of −2° C./minute.

Freezing the previously-activated NK cells at a particular cooling rate may be achieved using well-known apparatuses in art, e.g., programmable controlled rate freezing systems.

For example, commercial devices for cooling cells for cryopreservation may accomplish controlled temperature changes by injecting liquid nitrogen vapor into the device. As the temperature inside the devices increases or decreases, additional liquid nitrogen may be injected to maintain the desired cooling rate. Alternatively, the activated NK cells may be frozen in a mechanical freezer. The activated NK cells may be frozen as described herein or according to any protocol known to an ordinarily skilled artisan, e.g., at −135° C., liquid nitrogen vapor, etc.

In one embodiment, the activated NK cell population may be cryopreserved in a cryocyte bag (e.g., the activated NK cell population may be frozen at a cell density of $1-2 \times 10^7$ cell/mL) in a medium (e.g., a medium comprising X-vivo 10 (VWR, West Chester, Pa.), dimethyl sulfoxide (DMSO), and human serum albumin (HSA) at a ratio of 45(X-vivo):10 (DMSO):45(HSA)) and vacuum-wrapped in nitrogen vapor at or below −135° C. in a monitored nitrogen refrigerator.

In contrast to LAK cells, which typically lose their activated state after about 12 hours of preservation in the absence of IL-2, preservation of the activated NK cells of the present invention surprisingly does not affect the activation state of the cells, even if said preservation is in the absence of the activating agent. In one embodiment, preservation may occur in excess of 12 hours, more generally in excess of 12 to 18 hours, and preferably in excess of 24 to 36 hours. In one embodiment, the activated NK cell populations described herein may be cryopreserved (e.g., in nitrogen vapor) for at least about 1 day, e.g., for at least about 1 week, e.g., for at least about 4 weeks, e.g., for at least about 3 months, e.g., for at least about 6 months, e.g., for at least about 1 year, e.g., for at least about 5 years, etc.

After preservation, the cell population may be prepared for administration to a patient. Thawing of frozen cells may be accomplished according to well-known methods. General thawing procedures involve rapidly transferring the frozen cells to a 37° C. water bath and providing gentle agitation until the activated NK cells are completely thawed. After thawing, the thawed NK cells may be prepared for administration into a patient by adding, preferably in a dropwise fasion, pharmaceutically acceptable carriers at room temperature, e.g., to dilute the concentration of freeze medium and/or wash the previously activated NK cells. As demonstrated herein, the cell populations of the present invention retain their activated state after such preservation and without continued and/or subsequent exposure to the activating agent. As such, in one embodiment, the cells are prepared for administration in the absence of the activating agent. Preparation of the cells for administration after preservation depends on the preservation method. For example, cells may be prepared for administration after preservation by cell culture and/or refrigeration by one or more of the following: washing the cells, resuspending the cells in a pharmaceutically acceptable carrier, and/or containing the cells in suitable delivery device, e.g., a syringe. In one embodiment, cells are prepared for administration after cryopreservation by thawing, e.g., by gentle agitation in a 37° C. water bath and then containing the cells in a suitable delivery device, e.g., a syringe. These thawed cell populations may be surprisingly employed in the clinic almost immediately on an as-needed basis, e.g., without reactivation or other extensive and/or time-consuming manipulation. Accordingly, although unnecessary, cells prepared for administration after cryopreservation may be further prepared by the addition, preferably in a dropwise fashion, a pharmaceutically acceptable carrier at room temperature to, e.g., dilute the concentration of and/or wash the cells free of freeze medium.

In preferred embodiments, the pharmaceutically acceptable carrier is substantially free of an activating agent. In one embodiment, therefore, the invention provides a method for making a ready-to-use medicament in the form of an infusible formulation which is free of agent for activating NK cells, the method comprising, or consisting of, thawing cryopreserved activated NK cells substantially free of activating agent, the formulation being for use in treating a cancer without reactivation with and/or co-administration (whether simultaneous, separate or sequential) of the activating agent. The infusible formulation of this embodiment is ready for immediate use without any further processing.

Compositions

Accordingly, disclosed herein is a pharmaceutical composition comprising activated NK cells and a pharmaceutically acceptable carrier or medium that is substantially free of the activating agent. The activated NK cells exhibit durable and prolonged activity, and retain their activated state even after preservation. The activated NK cells may be previously preserved activated NK cells. In preferred embodiments, the subject activated NK cells overexpress CD69 and/or CD25 in comparison with resting NK cells and, more preferably, lose expression of CD16 and gain expression of CD15 as a result of activation.

As described herein, the activated CD69+CD25+CD16$^{low}$CD15+NK cells of the subject invention may, in contrast to LAK cells, be prepared for administration immediately after preservation, i.e., do not require reactivation, and do not require co-administration of the activating agent either simultaneously or sequentially. Accordingly, in one embodiment, the pharmaceutical composition comprises activated NK cells prepared for administration in a pharmaceutically acceptable carrier or medium that is substantially free of activating agent.

In one embodiment, the activated NK cells may comprise or consist essentially of autologous and/or allogeneic NK cells with respect to the recipient. In other words, autologous NK cells may be obtained from peripheral blood of the recipient. Allogeneic NK cells may be partially or fully HLA mismatched, and may be obtained from peripheral blood from a donor individual, or multiple donors.

Peripheral blood mononuclear cells may be collected by standard techniques (e.g. conventional apheresis). To minimize the possibility of graft versus host disease and immune mediated aplasia, allogeneic cells may be depleted of T cells. For example, the cell preparation may be depleted of CD3+ T-cells using microbeads conjugated with monoclonal mouse anti-human CD3 antibody and a cell selection device (such as the Miltenyi Biotec CliniMACS® cell selection device).

However, NK cells produced by such "negative selection" procedures alone do not have a high degree of purity and may be contaminated with T and B cells. Although not necessary in the autologous setting, removal of such cells is advantageous in the allogeneic settings contemplated herein. In order to reduce contamination, it is possible to obtain an NK cell preparation by direct immunomagnetic separation, for example on the basis of CD56 expression. To further reduce T cell contamination, the product may be depleted for CD3+ cells (for example using CD3 FITC and anti-FITC beads).

Prior to activation by the activating agent, the NK cell preparation may comprise at least 80%, at least 90%, at least 95% or at least 98% CD56+ cells. In another embodiment, prior to activation by the activating agent, the NK cell preparation may comprise less than 15%, less than 10%, less than 5% or less than 3% CD3+ cells. A skilled artisan will recognize that in an autologous setting, T cell content is irrelevant, and as such, non-selected NK cells may be used.

The CD69+CD25+CD16$^{low}$CD15+ activated NK cells of the subject invention surprisingly retain their activated state even after preservation and in the absence of the activating agent, and thus, do not need reactivation and/or subsequent contact with the activating agent prior to or during medical use. Accordingly, the pharmaceutical compositions disclosed herein comprise such previously-activated NK cells in pharmaceutically acceptable carriers that are substantially free of the activating agent. The subject NK cells exhibit prolonged activity (i.e., retain their activated state after preservation in the absence of the activating agent) despite preservation by, e.g., cell culture, cryopreservation, refrigeration, and the like.

In one embodiment, a pharmaceutical composition disclosed herein comprises a thawed cell population comprising activated NK cells that retain their activated state after preservation in the absence of the activating agent, and a pharmaceutically acceptable carrier, wherein the thawed cell population comprises a pharmacologically effective amount of activated NK cells for the treatment of cancer.

The amount of the cells needed for achieving a therapeutic effect may be determined empirically in accordance with conventional procedures for the particular purpose. Generally, for administering the cells for therapeutic purposes, the cells are given at a pharmacologically effective dose. By "pharmacologically effective amount" or "pharmacologically effective dose" is an amount sufficient to produce the desired physiological effect or amount capable of achieving the desired result, particularly for treating the disorder or disease condition, including reducing or eliminating one or more symptoms or manifestations of the disorder or disease. As an illustration, administration of cells to a patient suffering from cancer provides a therapeutic benefit not only when the underlying condition is eradicated or ameliorated, but also when the patient reports a decrease in the severity or duration of the symptoms associated with the disease. Therapeutic benefit also includes halting or slowing the progression of the underlying disease or disorder, regardless of whether improvement is realized. Pharmacologically effective dose, as defined above, will also apply to therapeutic compounds used in combination with the cells, as further described below.

The pharmaceutical compositions will generally comprise a pharmaceutically acceptable carrier and a pharmacologically effective amount of the subject CD69+CD25+CD16$^{low}$CD15+ NK cells. The pharmaceutical composition may be generally formulated as solutions, suspensions, aerosols and other formulations known in the art.

As used herein, "pharmaceutically acceptable carrier" comprises any of the standard pharmaceutically accepted carriers known to those of ordinary skill in the art in formulating pharmaceutical compositions. Thus, the activated NK cells may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

While any suitable carrier known to those of ordinary skill in the art may be employed in the compositions, the type of carrier will typically vary depending on the mode of administration. The therapeutic compositions may be formulated for any appropriate manner of administration, including for example, oral, nasal, mucosal, rectal, vaginal, topical, intravenous, intraperitoneal, intradermal, subcutaneous, and intramuscular administration.

For parenteral administration, the compositions can be prepared for administration as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate.

The pharmaceutical compositions described herein may be presented in unit-dose or multi-dose containers, such as sealed infusion bags, ampoules or vials. Such containers are typically sealed in such a way to preserve the sterility and stability of the formulation until use. In general, formulations may be preserved as suspensions, solutions or emulsions in oily or aqueous vehicles, as indicated above. Alternatively, a pharmaceutical composition may be preserved in a freeze-dried condition requiring only the addition of a sterile liquid carrier immediately prior to use. In a preferred embodiment, a pharmaceutical composition is provided comprising the activated NK cells cryopreserved in a suitable cryopreservation medium, which can then be thawed and prepared as needed for administration to a patient.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease.

Determining the dosages and times of administration for a therapeutically effective amount are well within the skill of the ordinary person in the art. For example, an initial effective dose can be estimated from cell culture or other in vitro assays. A dose can then be formulated in animal models to generate a circulating concentration or tissue concentration, including that of the $IC_{50}$ as determined by the cell culture assays.

In addition, toxicity and therapeutic efficacy are generally determined by cell culture assays and/or using experimental animals, typically by determining a $LD_{50}$ (lethal dose to 50% of the test population) and $ED_{50}$ (therapeutically effectiveness in 50% of the test population). Guidance is found in standard reference works, for example, Goodman & Gilman's The Pharmacological Basis of Therapeutics, 10$^{th}$ Ed. (Hardman, J. G. et al., eds.) McGraw-Hill, New York, N.Y. (2001).

For the purposes of this invention, the methods of administration are chosen depending on the condition being treated and the form of the pharmaceutical compositions. Administration of the therapeutic compounds can be done in a variety of ways, including, but not limited to, subcutaneously, intravenously, intraperitoneally, intramuscularly, and possibly direct injection to specified organs such as e.g., spleen or bone marrow, although systemic administration is preferred. Administration of the pharmaceutical compositions may be through a single route or concurrently by several routes.

The compositions may be administered once per day, a few or several times per day, or even multiple times per day, depending upon, among other things, the indication being treated and the judgment of the prescribing physician. In a preferred embodiment, the cells are administered immediately after preservation Prior to treatment with the composition, the patient may receive some pre-treatment, for example, to de-bulk the tumor and/or immunosuppress the patient. This may be achieved, for example, by chemotherapy.

It is possible to obtain primary tumor cells from patients at time of diagnosis and to cryopreserve these as viable single cell suspensions. It is thus possible for a composition according to the invention to be tested in vitro against patient blasts. This could be done before embarking on a treatment regime, to gauge the suitability of the approach. The correlation of the results of the in vitro study and the corresponding clinical response to treatment may also be investigated.

The pharmaceutical compositions of the present invention may be used in medicine, e.g., in a medicament to treat or prevent a disease, e.g., cancer. Prior to treatment with the composition, the patient may receive some pre-treatment, for example, to de-bulk the cancer and/or to immunosuppress the patient, e.g., by chemotherapy.

Furthermore, activated NK cells prepared for administration in the absence of an activating agent may be used in the manufacture of a medicament for the treatment of such diseases.

Disease

The present invention is also based on the unexpected finding that an exogenous NK cells activated by an activating agent as disclosed herein, e.g., a CD15+ LAK-resistant tumor cell, may confer similar cytolytic activity to an endogenous NK cells. Accordingly, also described herein is a method of stimulating endogenous NK cell activity in a patient in need thereof, comprising administering to said patient a population of previously-activated NK cells that exhibit a durable and prolonged anti-tumor activity despite preservation, and advantageously, without the need for reactivation with co-administration of the activating agent itself, which raises potential toxicity and/or immunogenicity issues. In preferred embodiments, the activated NK cells are CD69+ and/or CD25+, and more preferably also CD15+ and CD16$^{low}$.

In one embodiment, the endogenous NK cell activity is anti-tumor activity. In another embodiment, cytolytic activity is conferred to an endogenous NK cell in a tumor-bearing host. In another series of embodiments, cytolytic activity is conferred to an endogenous NK cells in the presence of tumor cells, including tumor cell fragments. Such tumor cells, including tumor cell fragments, may originate from a primary tumor, metastases, or from an ex vivo source.

An ordinarily skilled artisan will recognize that that preserved population as described herein, as well as the method of stimulating endogenous NK cell activity, may be used to treat or prevent a disease or medical condition, in particular, cancer. There are about 200 different types of cancer. A list of types of cancer are well-known and available (for example, see the website for the Association of Cancer Online Resources, or the website for Cancer Research UK).

Some more common cancers include leukaemia (acute and chronic), bladder.cancer, bone cancer (osteosarcoma), Bowel (colorectal cancer), brain cancer, breast cancer, cervical cancer, oesophageal cancer, Hodgkin's lymphoma, kidney cancer, liver cancer, lung cancer, mesothelioma, multiple myeloma, nasopharyngeal cancer, non-Hodgkin's lymphoma, ovarian cancer, pancreatic cancer, penile cancer, prostate cancer, skin cancer (melanoma and non-melanoma) soft tissue carcinoma, gastric cancer, testicular cancer, thyroid cancer and endometrial cancer. In particular, the compositions disclosed herein may be useful to treat any cancer which is accessible to NK cells.

In one embodiment, the cancer may be a haematological malignancy, such as leukaemia (AML); Chronic lymphocytic leukemia (CLL); Lymphoma.

Myeloma is an incurable and fatal malignancy. NK activity against myeloma plasma cells is documented in vitro and enhanced NK activity against autologous myeloma cells has been shown to correlate with response to treatment with Thalidomide derivatives. Myeloma patients are generally young and fit enough to undergo autologous haematopoietic stem cell transplantation and could readily undergo a less invasive procedure such as the one provided by the present invention either alone or following autologous hematopoietic stem cell transplantation.

Post transplant lymphoproliferative disease (PTLD) is a serious and relatively common complication after solid organ transplantation and T cell immunotherapy is currently under trial with good success but is extremely expensive and technically difficult and thus restricted in its application. Therapy using NK cells activated according to the present invention therapy would be easy and safe in this group of patients.

In addition the composition may be used to treat solid tumors such as breast cancer.

The procedure is particularly suitable to treat "NK-resistant" tumors. Normal, non CD15+ LAK-resistant tumor cell-stimulated NK cells can spontaneously lyse some human tumors, but many other tumors are NK-resistant. "NK-resistant" as used herein, therefore, indicates tumor cells resistant to lysis by normal, non CD15+ LAK-resistant tumor cell-stimulated NK cells.

As explained above, inhibition of NK-mediated lysis is controlled by expression of specific MHC class I molecules on the target cell surface, particularly HLA-C. There are two distinct groups of HLA-C alleles with regard to NK cell recognition. Some tumors express both types of HLA-C allele, which is thought to make them resistant to NK-mediated lysis. "NK resistant" cells may, therefore express both groups of class I allele. Some leukemia/lymphoma-derived cell lines, such as Raji and Daudi express both types of HLA-C allele, making them useful models for NK-resistant tumor cells in vivo.

A patient administered with a pharmaceutical composition as disclosed herein may also be treated with other therapeutic agents. Preferred therapeutic agents include agents that enhance NK activity. Such enhancing agents are well known in the art. Non-limiting examples of such enhancing agents include thalidomide and its immunomodulatory (IMid) analogs (e.g., lenalidomide, Revlimid, CC-5013, CC-4047, ACTIMID; see, e.g., Wu et al. (2008) *Clin. Cancer Res.* 14:4650-7), cytokines (e.g., IL-2, IL-12, IL-15, CCL5), etc. The other therapeutic agents may be administered simultaneously or sequentially with the NK cells activated to exhibit durable activity as disclosed herein.

The invention will now be further described by way of the following non-limiting examples which further illustrate the invention, and are not intended, nor should they be interpreted to, limit the scope of the invention.

EXAMPLES

Example 1

Lewis X (CD15) Expression on Leukemic Cells Mediates Sustained Natural Killer Cell Priming and Tumor Lysis CTV-1, SEM, and MV-411 priming of NK cells leads to a sustained and durable activation state whereby activated NK cells retain the ability to lyse NK-resistant tumors even after preservation. Such activated NK cells prepared for administration after preservation offers an easy clinical application since such preparation does not require exposure to or reactivation with an activating agent.

Example 1.1

Materials and Methods

Example 1.1.1

Cell Lines and Cell Culture Reagents

All cell lines were obtained from the DSMZ, Braunschweig, Germany or from LGC, London, UK and cultured as recommended by the repository. The CTV-1 line was originally reported to be of myeloid origin, but has recently been shown to be an acute lymphoblastoid leukemia (ALL) with myeloid features that expresses CD15.

The SEM line is another CD15+ ALL line with the t(4;11) translocation.

MV-411 is a bi-phenotypic CD15+ t(4;11) acute myelomonocytic leukemia.

MOLT-16 and PF-382 are both CD15-ve ALL lines. The RAJI line is a B cell line derived from a non-Hodgkin lymphoma and is a prototypical NK-resistant line. K562 cells are prototypically NK-sensitive and are derived from an erythroblastoid leukemia. DU145 cells are derived from a prostate tumor epithelial cells, cultured as adherent cells and harvested by trypsinization at confluence. RPMI8226 cells are derived from a patient with myeloma. ARH77 cells are derived from the peripheral blood of a patient with plasma cell leukemia.

All cell cultures were maintained in Complete Media (CM) consisting of RPMI 1640 supplemented with 10% FCS, penicillin (100 i.u.) and streptomycin (100 i.u.) (all supplied by Invitrogen, Paisley, Scotland). All cells were maintained in continuous suspension culture and harvested in exponential growth phase prior to use a stimulator or target cells.

Example 1.1.2

Antibodies

Anti-CD15 antibody (clone MEM158), anti-CD49f antibody (clone 4F10) and anti-CD56 antibody (clone NCAM 16.2) were obtained from Serotec UK Ltd (Oxford, UK).

Example 1.1.3

Immunophenotyping

To analyze cell surface antigen expression, $10^5$ cells in 100 µl HBSS were incubated with fluorochrome conjugated monoclonal antibodies at the manufacturer's recommended concentration for 15 min at room temperature. After washing the cells were analyzed by flow cytometry (FACSCalibur with CellQuest software, Becton Dickinson, UK). Forward and side light scatter characteristics were used to gate on the viable lymphocyte population before acquisition of at least 10,000 cells from each sample. All fluorochrome conjugated mAbs were purchased from BDIS (Cowley, UK) or Beckman Coulter (High Wycombe, UK).

Example 1.1.4

Isolation of Human NK Cells and Tumor-Specific Activation

All samples were obtained with informed consent for research into innate immunity to leukemia. Fresh heparinised peripheral blood samples were obtained from normal healthy, volunteer donors. Peripheral blood mononuclear cells (PBMCs) were isolated from venous blood by discontinuous density gradient separation (Lymphoprep, Nycomed, UK) and suspended in CM at a concentration of $1\times10^6$ cell/mL. PBMC were incubated at a 2:1 stimulator:responder ratio with irradiated (30Gy) stimulator cells for up to 20 hours at 37° C. and in a 5% $CO_2$ atmosphere.

CD56+ or CD56+CD3-cells were purified from PBMC or PBMC:stimualtor cell co-cultures by direct immunomagnetic separation with CD56 Multisort kit (Miltenyi Biotec, Germany) with or without subsequent depletion with CD3 FITC and anti-FITC beads. All selected cells were confirmed as >98% CD56+ and, when CD3 depletion was performed, as <3% CD3+ and resuspended in CM. Immunoselection with anti-CD56 microbeads and subsequent washing removed all detectable stimulator cells from the final product.

Example 1.1.5

IL-2 Activation of NK Cells

Freshly isolated NK cells were suspended in CM with 100 i.u. IL-2 (Invitrogen, Paisley, UK) at a density of $1\times10^6$ cells/mL and incubated at 48 hours at 37° C. and in a 5% $CO_2$ atmosphere.

Example 1.1.6

Analysis of Intracellular Protein Phosphorylation by Flow Cytometry

Purified NK cells were pre-labelled with fluorochrome-conjugated anti-CD3 and anti-CD56 to allow identification of the cells when subsequently mixed with irradiated stimulator cells. Stimulator:responder cell mixtures were incubated at 37° C. for the prescribed periods and NK cell activation was stopped by addition of Cytofix buffer (BDIS, Oxford, UK) and incubation for 10 min. Permeabilisation was by ice-cold Perm Buffer III (BDIS, Oxford, UK) for 30 min followed by washing in Stain Buffer (BDIS, Oxford, UK) and resuspension in the same buffer. Samples were then incubated with the specific antibody to the phosphorylated protein of interest for 30 min at room temperature, washed twice and analyzed by flow cytometry (FACS Aria, BDIS, Oxford, UK). The percentage of cells expressing each antigen was determined using "cluster analysis" and the relative fluorescence intensity was calculated as median channel log fluorescence of the univariate "positive" population.

Example 1.1.7

Cytotoxicity Assay

Target cells in cytotoxicity assays included the NK-resistant RAJI cell line and the NK-sensitive K562 cell line (obtained from LGC cell bank). Target cells were recovered from suspension culture and washed in HBSS before resuspension in 1.0 ml of PHK-26 labeling diluent at a concentration of $4 \times 10^6$/ml. A 4 µl aliquot of PKH-26 was added to 1.0 ml of labeling diluent and then added to the cell suspension for 2 min at room temperature. The labeling reaction was stopped by the addition of 1.0 ml neat fetal calf serum for 1 min. Finally the labeled cells were washed twice in CM and resuspended in CM at $10^6$/ml. Fifty thousand PKH-26 labeled target cells in 100 µl RPMI 1640 (10% FCS) were added to 400 µl of effector cells (E:T ratio 1:1 or 5:1 as indicated in Figure legends since these are ratios which can be obtained in a clinical therapeutic setting without recourse to ex-vivo proliferation) and pelleted at 200×g for 1 min.

Cytotoxicity was measured in triplicate samples using a 4-hr cytotoxicity assay at 37° C. After the incubation period, the cells were resuspended in a solution of To-Pro-3 iodide (Invitrogen, Paisely Scotland) in PBS (1 and analyzed by flow cytometry. At least $1 \times 10^4$ target cells were acquired with 1024 channel resolution after electronic gating on red fluorescence and the mean proportion of To-Pro iodide positive cells from the triplicate samples determined. Background target cell death was determined from cells incubated in the absence of effector cells. Cell-mediated cytotoxicity was reported as percentage killing over background cell death averaged from the three samples (specific lysis):

Mean (% cell lysis in test–% spontaneous lysis).

Less than 5% spontaneous lysis of target cells was observed in these experiments. In some experiments the labeling strategy was reversed, with the effector cells being labeled with PKH-26 and analysis of cell lysis being restricted to the PKH-ve fraction. This reversal confirmed that initial findings were not due to an artifact of cell labeling.

Example 1.1.8

Generation of CD15-Transduced RAJI Cells

The cDNA encoding human α1,3-Fucosyltransferase IV (FUT4), which is responsible for the expression of CD15 (Nakayama, et al. (2001) *J. Biol. Chem.* 276:16100-106) was blunt ended PCR cloned into pLenti6/V5 (Invitrogen, Paisley, UK) from lymphocyte cDNA (a gift from Dr. Steve Hart) using the forward primer
5'ATG GGG GCA CCG TGG GGC TCG CCG AC3' (SEQ ID NO:1) and
5'AGT GGC GAG CTT GGT CGA CCG GTT3' (SEQ ID NO:2) and verified by sequencing to give pLenti6/CD15.

VSV-G pseudotyped virus was produced from 293T cells after transfection with pCMVDR8.91 (Zufferey et al. (1997) *Nat. Biotechnol.* 15:871-75) pVSV-G (Chan, et al. (2006) *Mol. Therapy* 11:120-31) and pLenti6/CD15 at ratios of 3.5: 1.75:5 using calcium phosphate. Twenty-four hours post transfection serum-supplemented medium was replaced with serum free medium and the virus harvested and concentrated by calcium precipitation 48 hours later. Viral supernatant was concentrated to a pellet and resuspended in 1 ml of buffer (100 mM EDTA, 50 mM NaCl, 0.2% BSA, pH 6.5). $10^6$ RAJI cells were cultured with $5 \times 10^5$ pfu for six hours before being pooled, washed and resuspended at $5 \times 10^5$/ml in fresh RPMI+ 10% FCS in a flask. CD15 expression was assessed 48 h post infection by flow cytometry.

Example 1.1.9

Statistical Analyses

Data for comparative statistical analysis were assessed for normality (Gaussian distribution) and thence for comparable variance by F-test (using GraphPad Prism v4.0). Distributions with equal variance were tested for significant difference of their means by Student t-test. Those with significantly different variance were tested by Snedecor's modified t-test which compensates for unequal variance. No data sets were non-Gaussian.

Example 1.2

Results

The regulation of human NK-mediated lysis of tumor cells involves a myriad of cell surface receptors on both the NK and tumor cells providing inhibitory and activatory signals. Lysis occurs when the combination of activation signals overcomes any inhibitory signals provided by ligands on the target cell. The principal ligands for inhibitory molecules appear to be the HLA class I antigens and susceptibility of tumors to NK mediated lysis has been shown to be related to the degree of expression of these molecules (Ciccone, et al. (1992) *J. Exp. Med.* 176:963-71). In contrast, the non-susceptibility to NK mediated lysis of the B lymphoma cell line RAJI has been attributed to its expression of all of the known classes of ligands for NK inhibitory molecules. Nonetheless, RAJI cells are susceptible to lysis by IL-2 or IL-15 activated NK cells, implying that the trigger ligands for NK activity are present at sufficient levels if the inhibitory signals can be overcome.

Bryceson and colleagues (2006) used the murine mastocytoma cell line P815 to test NK activating ligands in reverse cytotoxicity assays using resting, freshly isolated human NK cells, rather than NK lines or clones (*Blood* 107:159-66). These data confirmed that the lack of NK inhibition by HLA is not sufficient to trigger lysis (Warren et al. (1996) *J. Immunol.* 156:2866-73); P815 cells do not express HLA but are resistant to human NK lysis. Furthermore, apart from CD16, the other known NK triggering ligands require at least one co-ligation event to trigger cytokine secretion and/or lysis. The group did not investigate whether the two signals required needed to be delivered simultaneously or could be provided sequentially. Previous work has shown that an NK-resistant cell line which is also resistant to lysis by IL-2 activated NK cells is able to prime resting NK cells to lyse RAH cells (North, et al. (2007) *J. Immunol.* 178:85-94).

NK cells are an extremely important part of human defense against tumorigenesis and appear to play a critical role in ongoing tumor surveillance in healthy individuals (Imai, et al. (2000) *Lancet* 365:1795-99). They are highly conserved phylogenetically in that cytotoxic cells expressing perforin, granzymes and even CD16, CD56, CD57 and CD158b have been reported in the haemocoel of invertebrates (Lin, et al. (2001) *J. Exp. Zoology* 290:741-50; de Eguileor, et al (2002) *Curr. Pharmaceutical Design* 8:99-110); organisms which do not express the HLA molecules which are ligands for the inhibitory molecules such as CD158b. This suggests that the most fundamental control mechanisms for NK cells may not be inhibition through self-MHC but may be through a requirement for sequential or simultaneous activation signals akin to the co-stimulation and triggering of T cells in higher vertebrates. The data from Bryceson et al (2006) and North et al. (2007) support this hypothesis and the results presented here are the first to demonstrate the critical importance of the expression of a ligand for NK costimulation on a tumor cell in the initiation of lysis.

CD15-associated CD2L is required for NK-mediated lysis of NK-sensitive K562 erythroblastoid leukemia cells by resting NK cells but is not itself sufficient to prime NK cell activity since resting, normal human monocytes which express CD15 are unable to stimulate NK activity. Thus, some form of tumor-restricted signal(s) must be delivered to resting NK cells in the presence of co-stimulation to prime them to lyse tumor cells which present appropriate triggering ligands. Many candidate molecules for providing tumor-restricted signals have been proposed previously including heat shock proteins, lectins and complex carbohydrates but the essential ligands remain elusive. CTV-1 cells would appear to be a valuable tool in the further dissection of these ligands since it is clear that the simple lack of ligands for inhibitory receptors and presence of appropriate adhesion molecules is not sufficient for NK cell cytotoxicity of tumor cells.

The maintenance of the primed state in NK cells following removal of the priming tumor cell lines is a unique observation which contrasts sharply with the requirement for continuous cytokine exposure for the generation and maintenance of lymphokine activated NK cells. Here it is demonstrated that NK cells can be primed by a short period of co-incubation with relevant NK-resistant tumor cells which can then be removed with no effect on the primed state. These primed NK cells retain the ability to lyse NK-resistant tumors after cryopreservation and thawing allowing easy translation to clinical application since the cells can be prepared remotely and quality assured before release.

Example 1.2.1

CD15+ Leukemic Cells Prime Lysis of NK-Resistant Tumor Cells

Figure 1B:
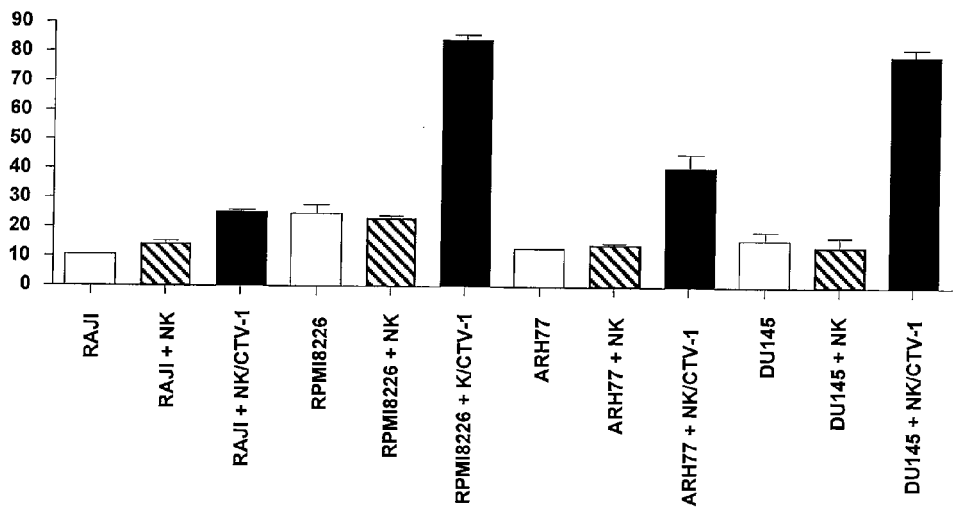
FIG. 1B shows the lysis (% specific lysis; y-axis) of NK-resistant RAJI cells (RAJI; x-axis), an NK-resistant myeloma (RPMI8226; x-axis), a plastocytoma (ARH77; x-axis), or an epithelial tumor cell line (DU145; x-axis) by resting NK cells (+NK; x-axis) or NK cells primed with CTV-1 cells (+NK/ CTV-1; x-axis).

Resting NK cells which had been co-incubated with NK-resistant CD15+ tumor cells (CTV-1, MV-411, SEM) lysed RAJI cells (FIG. 1A) and were capable of lysing a variety of NK-resistant tumor cells of different lineages including RPMI8226, ARH77, and DU145 (FIG. 1B). In contrast, resting NK cells or NK cells incubated with CD15-ve cells (MOLT-16, PF-382) were unable to lyse RAJI cells (FIG. 1A). Additionally, resting NK cells were unable to lyse ARH77 and DU145 cells (FIG. 1B). CTV-1 activated NK cells were also able to lyse allogeneic primary tumor cells isolated from tissue resected from patients with breast cancer and ascites from patients with ovarian cancer (data not shown; North et al. (2007) *J. Immunol.* 178:85-94).

Example 1.2.2

Anti-CD15 Blocks NK Priming

Figure 2A:
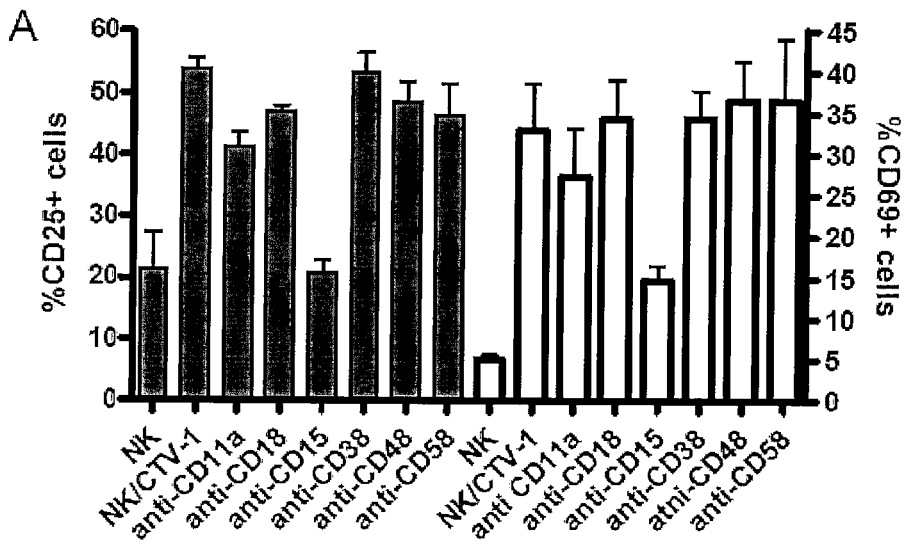
FIG. 2A shows the percentage of human NK cells expressing CD25 (% CD25+ cells—black bars; y-axis) or CD69 (% CD69+ cells—white bars; y-axis) after resting human NK cells from healthy volunteer donors (n=4) were incubated overnight alone (NK; x-axis) or with CTV-1 cells in the absence (NK/CTV-1; x-axis) or presence of anti-CD11a antibody (anti-CD11a; x-axis), anti-CD18 antibody (anti-CD18; x-axis), anti-CD15 antibody (anti-CD15; x-axis), anti-CD38 antibody (anti-CD38; x-axis), anti-CD48 antibody (anti-CD48; x-axis), or anti-CD58 antibody (anti-CD58; x-axis). The bars represent the mean percentage±SD of 3 replicates for each sample.

It was hypothesized that resting NK cells need two signals to initiate lysis and that these signals could be delivered sequentially since the priming tumor cell was absent from the NK:RAJI co-culture. CTV-1 cells were screened for potential NK-activating ligands with 58 different monoclonal antibodies (data not shown) and 5 candidate molecules were identified: CD58, CD48, CD38, CD15 and CD11a/CD18 complex. Of these only CD15 significantly (p<0.01) suppressed the activation of NK cells following CTV-1 co-incubation (FIG. 2A) as measured by CD25 and CD69 expression.

Figure 2B:
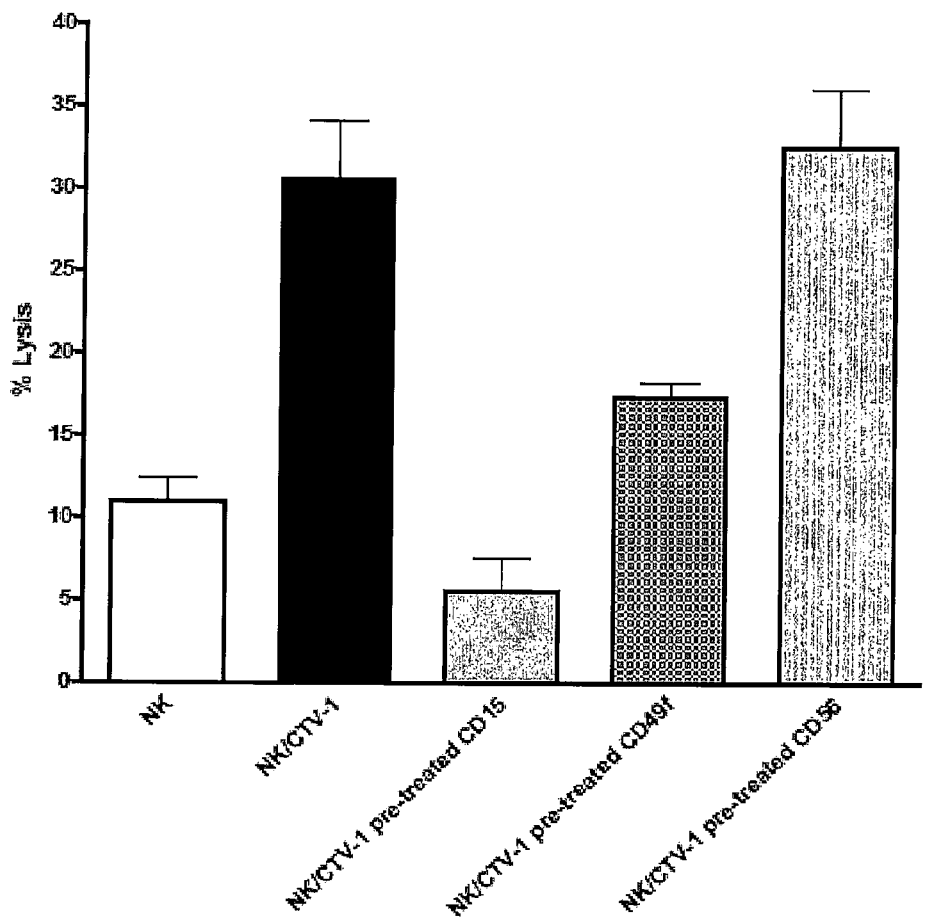
FIG. 2B shows the lysis of NK-resistant RAJI cells (% lysis; y-axis) by NK cells from normal volunteer donors (n-5) incubated for 20 h alone (NK; x-axis), with untreated CTV-1 cells (NK/CTV-1; x-axis), CTV-1 cells treated with saturating concentrations of anti-CD15 antibody (clone MEM 158-Serotek UK Ltd) (NK/ CTV-1 pre-treated CD15; x-axis) at saturating concentrations; CTV-1 cells pre-treated with saturating concentrations of anti-CD49f (clone 4F10-Serotek UK Ltd) (NK/CTV-1 pre-treated CD49f; x-axis); or CTV-1 cells pre-treated with saturating concentrations of anti-CD56 (clone NCAM 16.2-BDIS, UK) (NK/CTV-1 pre-treated CD56; x-axis). The bars represent the mean percentage±SD of 3 replicates for each sample.

In a search for priming signal receptors on the NK cells, CD2 was identified as a potential candidate although blockade of its common ligand CD58 on the priming cell did not significantly inhibit lysis. However, over ten years ago, Warren and colleagues (1996) had described a moiety within the CD15 epitope of Lewis' which is a ligand for CD2 and which is present on the prototypical NK target cell, K562 (*J. Immunol.* 156:2866-73). Furthermore, they found that its expression on K562 was required for NK-mediated lysis; absence of HLA class I expression was not sufficient to trigger lysis. CD2 is a known co-stimulatory priming molecule on resting NK cells The NK-priming cell line, CTV-1, which expresses high levels of CD15 and co-incubation of NK cells with CTV-1 leads to transfer of the CD15 onto the NK cells (data not shown) akin to the transfer of MICA which has been reported (McCann, et al. (2007) *J. Immunol.* 178:3418-26) suggesting that it is an important constituent of the NK:CTV-1 immune synapse. The ability of anti-CD15 to block NK priming was tested in cytotoxicity assays. The prototypical NK-resistant RAJI cell is sensitive to NK-mediated lysis after priming through contact with CTV-1. Resting human NK cells co-incubated with CTV-1 in the presence or absence of blocking antibodies for 20 hours and tested in 4 hour killing assays against RAJI cell targets. Two anti-CD15 mAbs were used, clone LeuM1 (BDIS, Oxford, UK) and clone MEM158 (Serotec, Oxford, UK) the former having been reported to bind a site within CD15 which excludes the CD2-L site (Warren, et al. (1996) *J. Immunol.* 156:2866-73). Anti-CD15 clone MEM158 significantly reduced the NK activity (FIG. 2b), indeed to a level below that of anti-CD49f, the positive inhibitory control (Lowdell, et al. (1994) *Exp. Hematol.* 23:1530-34). It was extremely interesting to note that lysis of the prototypical NK-sensitive cell line, K562 also required CD15-NK interaction. K562 cells express high levels of CD15 and blockade of this antigen with MEM158 substantially inhibited lysis by resting NK cells (FIG. 3) further supporting its central role in NK cell priming and confirming that "missing self" alone is inadequate for induction of lysis by resting human NK cells.

Example 1.2.3

Transfection of CD15 into NK-Resistant Cells Provides the Priming Signal

Figure 3:
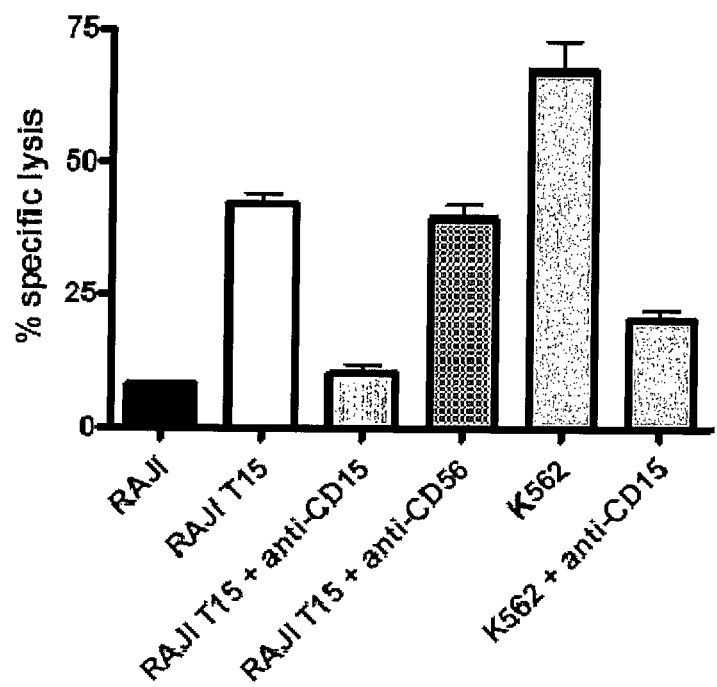
FIG. 3 demonstrates that transfection of NK-resistant RAJI cells with FUT4 renders the cells susceptible to NK-mediated lysis. The bars in FIG. 3 represent the mean percentage specific lysis±SD (% specific lysis; y-axis) by resting NK cells of unmodified RAJI cells (RAJI; x-axis), CD15+ RAJI cells (RAJI T15; x-axis); CD15+ RAJI cells pre-treated with anti-CD15 antibody (RAJI T15+anti-CD15; x-axis); CD15+RAJI cells pretreated with anti-CD56 antibody (RAJI T15+anti-CD56), K562 cells (K562); and K562 cells pre-treated with anti-CD15 antibody (K562+anti-CD15). Effector:Target ratios were 5:1 for all experiments (n=3).

Confirmation of the role of CD15 was achieved through transfection of RAJI cells with the cDNA for FUT4. Transfection of FUT4 into RAJI cells led to expression of CD15 within 48 h and rendered the cells susceptible to lysis by resting NK cells (FIG. 3). This was blocked effectively by addition of saturating concentration of anti-CD15 during the cytotoxicity assay (FIG. 3). Addition of anti-CD2 mAbs neither blocked nor enhanced the effect, suggesting that these mAbs did not bind to the appropriate epitope (data not shown).

Example 1.2.4

Figure 4:
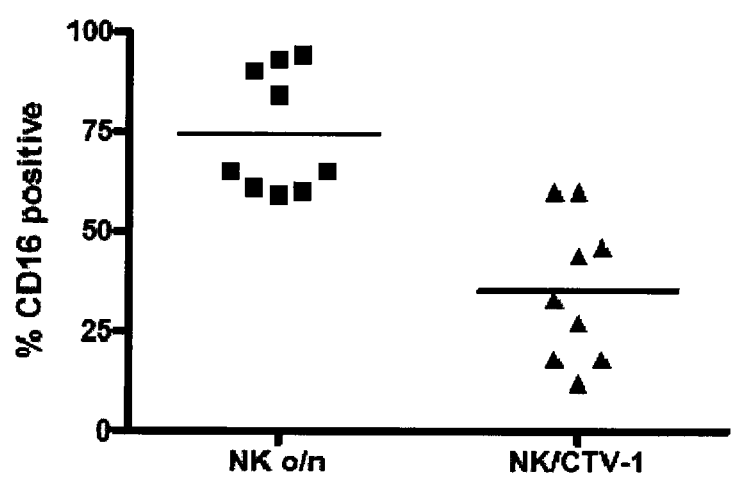
FIG. 4 demonstrates that tumor-mediated NK priming is associated with loss of surface expression of CD16.
Figure 5A:
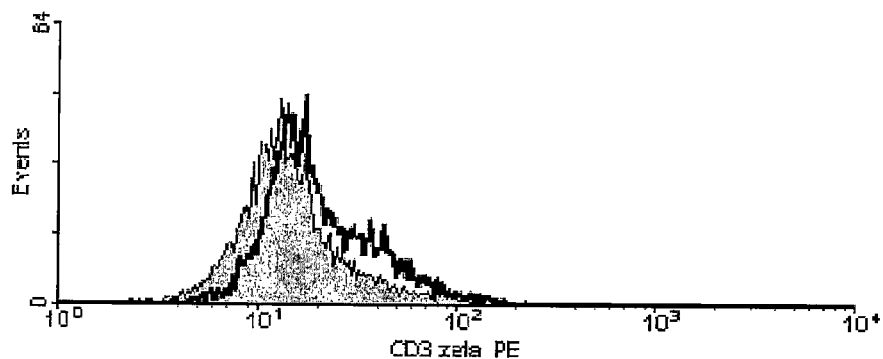
FIG. 5A shows the number of NK cells (events; y-axis) with phosphorylated CD3ζ (CD3 zeta PE; x-axis) as determined by flow cytometric analysis after resting NK cells were stimulated for 10 minutes with RAJI cells (filled histogram) or CTV-1 cells (non-filled histogram) and then fixed.
Figure 5B:
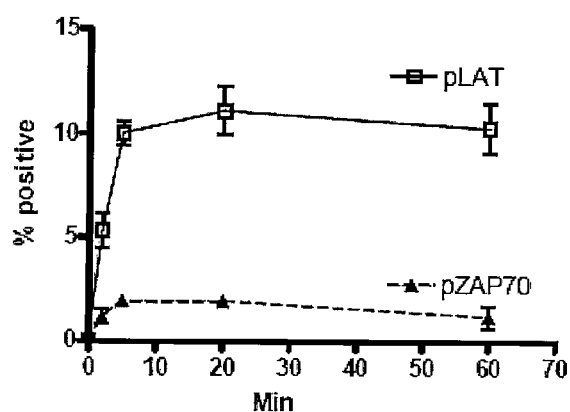
FIG. 5B shows the mean percentage±SD of human NK cells (% positive; y-axis) with phosphorylated LAT (pLAT; □) or phosphorylated ZAP70 (pZAP70; ▲) at time points (min; x-axis) after stimulation with CTV-1 cells at a stimulator:responder ratio of 2:1 as determined by flow cytometric analysis (n=3).

CD2 Ligation Via the CD15 Associated Ligand Induces Synthesis of Gamma Interferon Via the LAT-STAT Signalling Cascade Evidence to support the hypothesis that CD15 is involved in the ligation of CD2 was provided by the antibody blocking experiments and the demonstration of phosphorylation of CD3ζ. In contrast to CD2 on T cells, CD2 on NK cells is not constitutively associated with CD3ζ. Cytoplasmic CD3ζ is bound to CD16 in NK cells (Moingeon, et al. (1991) *Proc. Natl. Acad. Sci.* 89:1492-96) which, presumably explains the unique ability of CD16 to activate and trigger resting human NK cells (Bryceson, et al. (2006), supra). Conjugation of resting NK with CTV-1 leads to rapid shedding of extracellular CD16 (FIG. 4; North, et al. (2007), supra) and it was hypothesized that this might facilitate the interaction of the cytoplasmic CD16/CD3ζ complex to associate with the intracellular domain of CD2 (Moingeon, et al. (1992), supra). As shown in FIG. 5A, co-incubation of resting NK cells with CTV-1 cells induced rapid phosphorylation of CD3ζ. CD2 ligation has been shown to lead to phosphorylation of LAT (Inoue, et al. (2000) *Eur. J. Immunol.* 32:2188-98) and flow cytometric analysis of intracellular phosphorylation of LAT and ZAP-70 demonstrated rapid phosphorylation of LAT in the absence of ZAP-70 phosphorylation (FIG. 5B) confirming ligation of CD2 by CD2L within CD15 on the CTV-1 cells. Phosphorylation of LAT is thought to be via phosphorylation of ZAP70 but consistent pZAP70 upon CTV-1 coculture or following crosslinkage with the available anti-CD2 antibodies was not demonstrable (data not shown). In contrast, cross-linkage of CD3 on T cells led to rapid and sustained pZAP70 (data not shown). This suggests that CD2-mediated LAT phosphorylation in NK cells may be independent of pZAP70.

Figure 5C:
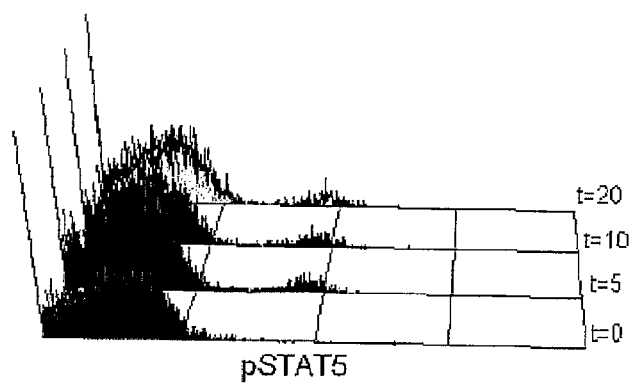
FIG. 5C shows the number of NK cells (y-axis) with phosphorylated STAT5 (pSTAT5; x-axis) after resting NK cells were stimulated with CTV-1 cells for 0 minutes, 5 minutes, 10 minutes or 20 minutes.
Figure 6A:
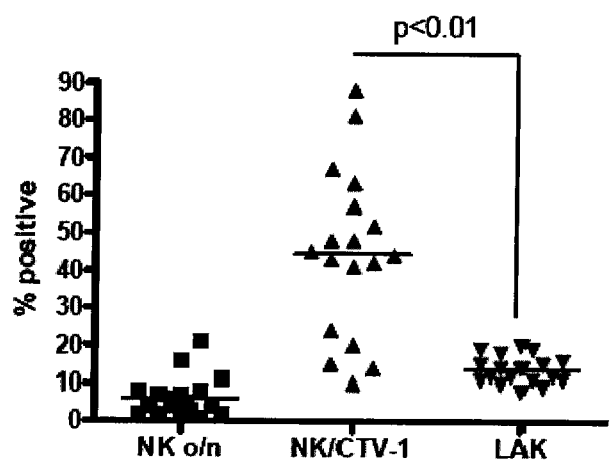
FIG. 6A shows the percentage of NK cells positive for CD25 expression (% positive; y-axis) after incubation overnight in the absence of any activated agent (NK o/n; x-axis), in the presence of CTV-1 cells (NK/CTV-1; x-axis) at a 1:2 ratio, or in the presence of IL-2 (100 i.u./mL) (LAK; x-axis) for 48 h. Parallel cultures were labeled for surface expression of Cd69 and intracellular IFN-γ.
Figure 6B:
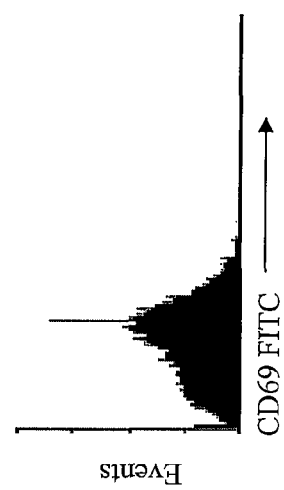
Figure 6C:
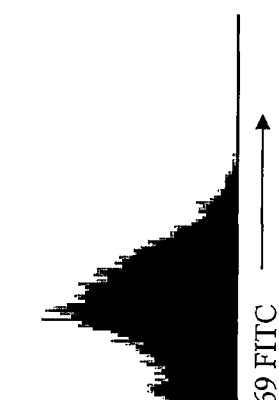
Figure 6D:
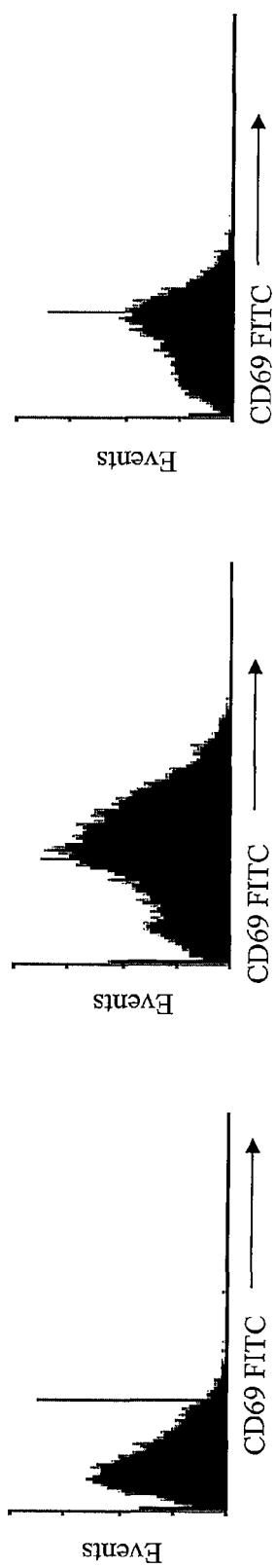
Figure 6E:
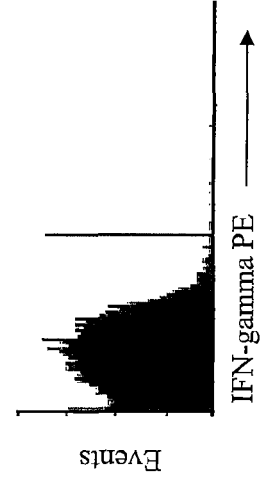
Figure 6F:
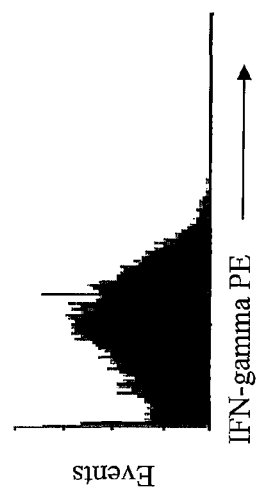

One of the known outcomes of CD2 signalling is the phosphorylation of STATS which can lead to interferon-gamma synthesis in NK cells (Gonsky, et al. (2004) *J. Immunol.* 173:6241-47). Indeed, pSTAT5 was detectable within 5 minutes and sustained for at least 20 minutes of co-incubation of CTV-1 cell lysates with resting NK cells (FIG. 5C) and was associated with upregulation of CD25 (FIG. 6A) and CD69 (FIG. 6C) and increased synthesis of interferon-gamma within 4 h (FIG. 6F). Activation of NK cells with SEM or MV4-11 cells also resulted in rapid upregulation of cell surface expression of CD25 and CD69 by the activated NK cells (data not shown). CD15-associated CD2L is required for NK-mediated lysis of the NK-sensitive erythroblastoid leukemia K562 by resting NK cells but is not itself sufficient to prime NK cell activity since resting, normal human monocytes which express CD15 are unable to stimulate NK activity. Thus some form of tumor-restricted signal(s) must be delivered to resting NK cells in the presence of costimulation to prime them to lyse tumor cells which present appropriate triggering ligands. Many candidate molecules have been proposed previously including heat shock proteins, lectins and complex carbohydrates. CTV-1 cells would appear to be a valuable tool in the further dissection of these ligands since it is clear that the simple lack of ligands for inhibitory receptors is not sufficient for NK cell cytotoxicity of tumor cells.

Example 1.2.5

Figure 6G:
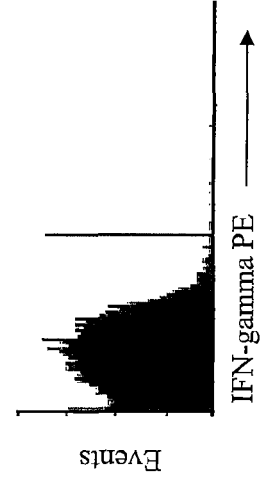

CD2-Mediated and IL-2 Mediated Activation of Resting NK Cells Operate by Different Pathways and have Different Physiological Outcomes In contrast to the CD3ζ-LAT-Stat pathway activated by CD2 ligation, IL-2 is known to activate NK cells via MKK1/1/ERK (Yu, et al. (2000) *J. Immunol.* 164:6244-51) and upregulation of CD69 and interferon synthesis takes a minimum of 48 hours (FIG. 6D and FIG. 6G, respectively). Upregulation of CD25 expression following IL-2 stimulation was also significantly slower than that induced by CD2 ligation by CTV-1 and the proportion of activating NK cells was consistently lower (FIG. 6A).

Example 1.2.6

CD2-Mediated NK Cell Priming is Stable after the Removal of the Priming Signal

Figure 7:
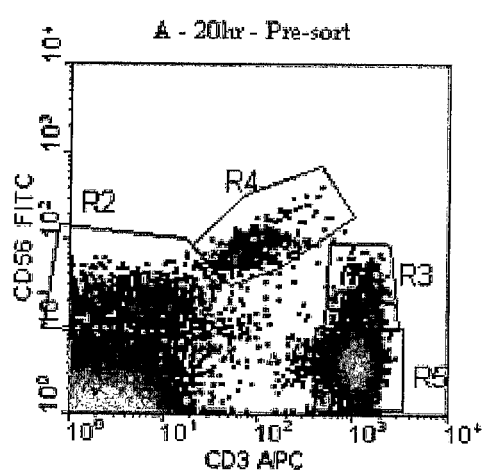
FIG. 7 shows that CTV-1 primed NK cells retain their primed state even after cryopreservation.
Figure 7:
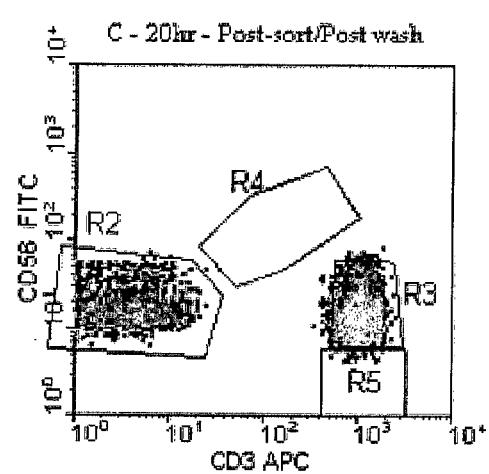
Figure 7:
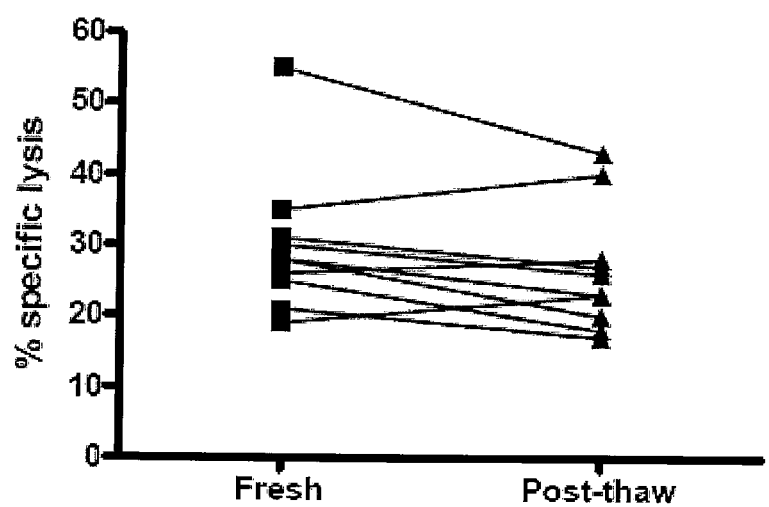

IL-2 activated NK cells rapidly return to the non-activated state upon removal of IL-2 and/or lose activity after preservation, particularly in the absence of IL-2. Lymphocytes from 10 normal donors were stimulated with a lysate of CTV-1 cells for 20 hours at a nominal CTV-1:NK cell ratio of 2:1. NK cells were then directly isolated by immunomagnetic selection with anti-CD56 microbeads (Miltenyi Biotec, Oxford, UK). The primed NK cell preparations were shown to be free from CTV-1 contamination (FIGS. 7A and 7B). The degree of RAJI cell lysis mediated by freshly isolated tumor-primed NK cells was not significantly different from matched cells which had been cryopreserved in nitrogen vapor for 14 days (FIG. 7C).

Example 2

Populations of Human NK Cells Primed by a Tumor Cell Line May be Prepared for Administration Immediately after Preservation and Safely Transplanted to Haploidentical Patients with AML and Lead to Demonstrable GvL and Long Term NK Chimerism A clinical trial in patients with AML in complete remission (CR) or partial remission (PR) with less than 25% blasts, but not candidates for a conventional transplant using sibling or alternative donors, was initiated.

Example 2.1

Materials and Methods

Example 2.1.1

Isolation and Activation of Human NK Cells

NK cells exhibiting a durable activation state were generated from a single apheresis of non-mobilized peripheral blood from a haploidentical family donor by overnight co-incubation of CD56+ NK cells (CliniMACS using anti-CD56 microbeads) with the lysate of CTV-1 tumor cells at a nominal stimulator:target ratio of 2:1. The NK cells were then purified from the lysate by density gradient separation and washing. Product release criteria included sterility, CD56+/CD3− NK cell dose within 5% of the prescribed dose and total CD3+/CD56− T cell dose of <$10^4$/kg.

Example 2.1.2

Preparation of Freeze Medium

Single dose aliquots of the activated NK cells were prepared, cryopreserved, and stored in a cord blood storage unit until used. Single dose aliquots (e.g., Dose 1: 1×$10^6$ CD56+ NK cells/kg) were cryopreserved in a DMSO/HSA mixture. The DMSO/HSA mixture was prepared by inserting the spike of a 600 mL transfer pack and two air-inlets into the rubber bung of a bottle of human albumin serum (HSA) 4.5% solution (ZENALB 4.5; Bio Products Laboratory, Hertfordshire, UK). After 150 mL of the HSA 4.5% was allowed to run into the 600 mL transfer pack, the transfer pack line was clamped, heat-sealed three times and broken off at the middle seal. After the spike of a coupler leur adaptor set was connected to a port of the HSA 4.5%-containing transfer pack and a three-way stopcock, the HSA 4.5% containing transfer pack was cooled by placement on a pre-cooled ice pack. With aseptic techniques, a 16G needle connected to a 50 mL syringe was used to aspirate 37.5 mL DMSO. After removal of the 16G needle, the 50 mL syringe was attached to the three-way stopcock attached to the HSA 4.5%-containing transfer pack. The 37.5 mL DMSO was transferred to the HSA 4.5%-containing transfer pack to obtain a freeze medium with a final concentration of 20% DMSO/HSA. The 20% DMSO/HSA freeze medium remained cooled on a pre-cooled ice pack during the cryopreservation procedure.

Example 2.1.3

Cryopreservation of Activated NK Cells

The freeze media as prepared in Example 2.1.2 was added to the required dose of NK cells to bring the cell volume to 17 mL, and the NK dose/freeze media mixture was transferred to one or more cryocyte bags (Catalog No. 200-074-401; Miltenyi Biotec, Surrey, UK). The spike of a Cryocyte manifold set 4S-4M60 (Origen, Austin Tex.) was inserted into the DMSO/HSA preparation bag while the leur adaptors of the Cryocyte manifold set were connected to the NK cell-containing Cryocyte bag(s). An equal amount of the DMSO/HSA freeze medium was added to the NK Cryocyte bag(s) and mixed gently, Air was removed from the Cryocyte bag(s). A 19G needle connected to a 5 mL syringe was used to aspirate 4.3 mL of the cell suspension for cell count, cell viability and sterility studies. The Cryocyte bag(s) were doubled bagged and placed into a Planer Kryo-560-16 controlled rate freezer (Cryo Solutions; the Netherlands) for cooling according to the freezing program. The freezing program, which is approximately 65 minutes, holds the cells at 4° C. for 5 minutes then cools the cells to −30° C. at a rate of −1° C./minute, and thereafter to −100° C. at a rate of −2° C./minute. After the completion of the freezing program, the cryopreserved NK cells were placed in a liquid nitrogen storage dewar in the vapor phase of liquid nitrogen at −135° C.

Example 2.1.5

Patient Characteristics: Described herein are the characteristics of the six patients treated at the first dose level ($1 \times 10^6$ NK cells/kg). Patient 1 is a 56 year old female who presented with AML. The patient was put into complete remission (CR) 1 with chemotherapy and gemtuzumab ozogamicin. The first relapse occurred and the patient was put into CR2 with chemotherapy, and after an unsuccessful search for an allogeneic donor, received an autologous transplant using busulfan IV/cyclophosphamide conditioning for bone marrow transplant. The patient subsequently relapsed and was referred to this clinical trial. Salvage therapy with high dose cytaribine put the patient into CR3. Patient 1 received $10^6$ activated NK cells/kg from her daughter.

Patient 2 is a 72 yr old male who presented with AML. After chemotherapy with low dose cytarabine and 4 courses of 5-azacytidine, the patient was in PR with 19% blasts in the bone marrow aspirate. No consolidation or salvage therapy was given and he was not a candidate for bone marrow therapy. This patient received $10^6$ activated NK cells/kg.

Patient 3 is a 52 yr old male who was diagnosed with AML (t9:11). He was put into CR1 with chemotherapy, but relapsed within a year. Salvage therapy with idarubicin carboplatin and etoposide put him into morphological, but not cytogenetic CR. He received a HLA-identical sibling bone marrow therapy after busulfan IV/cyclophosphamide conditioning, but relapsed again eight months later. He received idarubicin carboplatin and etoposide salvage therapy and was placed into CR3 before receiving $10^6$ activated NK/kg from a different sibling.

Each patient was conditioned prior to infusion with the activated NK cells. Patients were conditioned with Fludarabine (25 mg/m$^2$/day) for 3 days plus a single fraction (2Gy) total body irradiation (TBI) on day 4. On the day of NK cell infusion (day 0), the cryopreserved NK cells were prepared for administration at the patient's bedside. Briefly, cryopreserved NK cells were transported with a liquid nitrogen phase shipper at a temperature between about −135° C. and −190° C. The double-bagged NK cells were thawed in a waterbath of sterile saline set at 37° C. with gentle agitation. After demonstrating integrity of the bag, the outer cryocyte bag was removed to allow NK cell transfer to a syringe by attachment of the injeciton site coupler to a port in the inner bag and a 16G needle. A small aliquot of cells was removed and placed on ice for post-transfusion cell counts. The remaining NK cells were administered by IV within 10 minutes of thawing and without re-stimulation, by slow push.

Patients were monitored closely for safety and assessed with frequent laboratory and clinical evaluations. Bone marrow aspirate (BMA) was used to assess disease status and specialized studies to evaluate chimerism and NK cell function were performed periodically. The clinical study was completed for each patient at 6 months following NK cell infusion.

Example 2.2

Results

No infusional toxicity was observed. All patients suffered a degree of bone marrow suppression requiring in-patient supportive care, with aplasia ranging from 3 weeks up to 100 days. Patient 1 remains in CR at month+16 with stable blood counts and has returned to a fully active professional and personal life. Patient 2 achieved and remained in CR until month+11, relapsed and has been treated with second activated NK infusion. Patient 3 experienced prolonged and severe pancytopaenia requiring CD34-selected stem cell rescue and achieved and remained in CR until month+11.5. Currently patient 3 is undergoing re-induction chemotherapy in order to be treated with a second dose of activated NK cells. Extremely prolonged NK chimerism (up to +6 months) has been seen in all patients in the absence of donor T cell chimerism. The single patient receiving a second NK cell dose achieved donor NK engraftment without additional immune suppression

TABLE 1

| NK cell date | Relapse date | Patient # | alive | OS[1] (days) | LFS[2] (days) | 6 month CR |
|---|---|---|---|---|---|---|
| Jul. 31, 2008 | | 1 | yes | 617 | 617 | yes |
| Jan. 2, 2009 | Oct. 30, 2009 | 2 | yes | 462 | 301 | yes |
| Jan. 16, 2009 | Nov. 22, 2009 | 3 | yes | 449 | 311 | yes |

[1]OS = Overall Survival as of Apr. 9, 2010
[2]LFS = Leukemia free survival as of Apr. 9, 2010

The kinetics of activated allogeneic NK engraftment have been studied in Patient #01 and #03. NK cells were detected by FACS in the circulation at a maximum of 10% of the NK cell population by week 2 following NK cell infusion. Calculations suggested a 3 fold expansion of donor NK cell numbers in vivo. Low levels of allogeneic NK cells (about 1%) were detected for approximately 3 months, but there is no evidence of permanent engraftment. By 6 months, there were no circulating allogeneic NK cells detected in these patients.

CONCLUSIONS

Haploidentical donor NK cells prepared for administration immediately after preservation without subsequent exposure to or reactivation with an activating agent can be infused safely and, in general, lead to tolerable episodes of pancytopaenia. All patients have shown a degree of clinical response with resolution of residual disease in some patients and unexpectedly prolonged remission in others. The activated NK cells have engrafted and expanded in all patients. Enrollment continues.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A pharmaceutical composition for direct administration to a patient in need thereof without simultaneous, separate or sequential administration of an activating agent comprising activated NK cells in a pharmaceutically acceptable medium substantially free of activating agent, wherein said activating NK cells overexpress CD69 and CD25 in comparison with resting NK cells, and wherein said NK cells are CD15$^+$ and CD16$^{lo}$.

2. The pharmaceutical composition according to claim 1, wherein said activated cells have been previously preserved.

3. The pharmaceutical composition according to claim 1, wherein said pharmaceutical composition comprises NK cells that are autologous to the patient.

4. The pharmaceutical composition according to claim 3, wherein said pharmaceutical composition further comprises NK cells that are allogeneic to the patient.

5. The pharmaceutical composition according to claim 1, wherein said pharmaceutical composition comprises NK cells that are allogeneic to the patient.

6. The pharmaceutical composition according to claim 5, wherein said pharmaceutical composition comprises exogenous NK cells that are allogeneic to each other.

7. The pharmaceutical composition according to claim 1, wherein said activating agent is a CD15+ LAK-resistant tumor cell.

8. The pharmaceutical composition according to claim 7, wherein said tumor cell is selected from the group consisting of a CTV-1 cell, an MV4-11 cell, an SEM cell, combinations thereof, and sublines thereof.

9. The pharmaceutical composition according to claim 2, wherein said activated NK cells were preserved for more than 12 hours.

10. The pharmaceutical composition according to claim 9, wherein said activated NK cells were preserved for more than 24 hours.

11. The pharmaceutical composition according to claim 1, wherein said composition is for administration without co-administration of the activating agent.

12. A method of stimulating endogenous NK cell activity in a patient in need thereof, comprising administering the pharmaceutical composition according to any one of claims 1, 2-11 to said patient without simultaneous, separate or sequential administration of the activating agent.

13. The method of claim 12, wherein said patient is a tumor-bearing patient, and said endogenous NK cell activity is anti-tumor activity.

14. The method of claim 12, wherein the activated NK cells in said composition are preserved after activation and before administration to said patient.

15. The method of claim 14, wherein the activated NK cells in said composition remain substantially free of activating agent during and/or after preservation.

16. The method according to claim 15, wherein said preservation is cryopreservation.

17. The method according to any one of claims 12-16, wherein said activated NK cells are further characterized as CD69$^+$CD25$^+$CD16$^{lo}$CD15$^{+\ NK\ cells}$.

18. A method for making a ready-to-use medicament in the form of an infusible formulation which is substantially free of an agent for activating NK cells, comprising thawing a pharmaceutical composition according to any one of claims 1, 2-11 comprising cryopreserved activated NK cells substantially free of activating agent, the formulation being for use without simultaneous, separate or sequential administration of the activating agent.

* * * * *